(12) United States Patent
Yarmush et al.

(10) Patent No.: US 10,363,276 B2
(45) Date of Patent: Jul. 30, 2019

(54) COMPOSITIONS, METHODS, AND DEVICES FOR TREATING DISEASE

(71) Applicants: The General Hospital Corporation, Boston, MA (US); Massachusetts Institute of Technology, Cambridge, MA (US)

(72) Inventors: Martin Leon Yarmush, Newton, MA (US); Biju Parekkadan, Cambridge, MA (US)

(73) Assignees: The General Hospital Corporation, Boston, MA (US); Massachusetts Institute of Technology, Cambridge, MA (US)

(*) Notice: Subject to any disclaimer, the term of this patent is extended or adjusted under 35 U.S.C. 154(b) by 11 days.

(21) Appl. No.: 14/967,028

(22) Filed: Dec. 11, 2015

(65) Prior Publication Data

US 2016/0331784 A1   Nov. 17, 2016

Related U.S. Application Data

(63) Continuation of application No. 13/460,315, filed on Apr. 30, 2012, now abandoned, which is a continuation of application No. 11/871,071, filed on Oct. 11, 2007, now Pat. No. 8,172,784.

(60) Provisional application No. 60/995,316, filed on Sep. 26, 2007, provisional application No. 60/923,138, filed on Apr. 12, 2007, provisional application No. 60/851,234, filed on Oct. 12, 2006, provisional application No. 60/850,778, filed on Oct. 11, 2006.

(51) Int. Cl.
| | | |
|---|---|---|
| *A61M 1/34* | (2006.01) | |
| *A61M 1/36* | (2006.01) | |
| *C12M 1/00* | (2006.01) | |
| *A61K 35/28* | (2015.01) | |
| *C12N 5/071* | (2010.01) | |
| *C12N 5/0775* | (2010.01) | |
| *G01N 33/50* | (2006.01) | |

(52) U.S. Cl.
CPC ........... *A61K 35/28* (2013.01); *A61M 1/3472* (2013.01); *A61M 1/3489* (2014.02); *A61M 1/3687* (2013.01); *A61M 1/3689* (2014.02); *C12M 29/16* (2013.01); *C12N 5/067* (2013.01); *C12N 5/0663* (2013.01); *G01N 33/5067* (2013.01); *G01N 33/5073* (2013.01); *C12N 2502/1358* (2013.01); *G01N 2500/00* (2013.01); *G01N 2800/085* (2013.01)

(58) Field of Classification Search
None
See application file for complete search history.

(56) References Cited

U.S. PATENT DOCUMENTS

| | | |
|---|---|---|
| 4,833,083 A | 5/1989 | Saxena |
| 5,549,674 A | 8/1996 | Humes et al. |
| 5,605,835 A | 2/1997 | Hu et al. |
| 5,866,420 A | 2/1999 | Talbot et al. |
| 5,942,436 A | 8/1999 | Dunn et al. |
| 6,328,960 B1 | 12/2001 | McIntosh et al. |
| 6,372,494 B1 | 4/2002 | Naughton et al. |
| 6,372,495 B1 | 4/2002 | Flendrig |
| 6,429,012 B1 | 8/2002 | Kraus et al. |
| 6,472,200 B1 | 10/2002 | Mitrani |
| 6,561,997 B1 | 5/2003 | Weitzel et al. |
| 6,562,616 B1 | 5/2003 | Toner et al. |
| 6,582,955 B2 | 6/2003 | Martinez et al. |
| 6,607,501 B2 | 8/2003 | Gorsuch |
| 6,759,245 B1 | 7/2004 | Toner et al. |
| 7,160,464 B2 | 1/2007 | Lee et al. |
| 7,160,719 B2 | 1/2007 | Nyberg |
| 7,622,108 B2 | 11/2009 | Collins et al. |
| 7,670,596 B2 | 3/2010 | Collins et al. |
| 8,172,784 B2 | 5/2012 | Yarmush et al. |
| 2001/0033834 A1 | 10/2001 | Wilkison et al. |
| 2001/0034055 A1 | 10/2001 | Lee et al. |
| 2002/0188240 A1 | 12/2002 | Gorsuch |
| 2003/0017142 A1 | 1/2003 | Toner et al. |
| 2003/0180269 A1 | 9/2003 | Hariri |
| 2003/0228685 A1 | 12/2003 | Nyberg |
| 2004/0107453 A1 | 6/2004 | Furcht et al. |
| 2005/0008626 A1 | 1/2005 | Fraser et al. |
| 2005/0148073 A1 | 7/2005 | Hansen et al. |
| 2005/0182349 A1 | 8/2005 | Linde et al. |
| 2006/0003436 A1 | 1/2006 | DiMilla et al. |
| 2007/0065415 A1 | 3/2007 | Kleinsek et al. |
| 2007/0292399 A1 | 12/2007 | Heidaran et al. |

FOREIGN PATENT DOCUMENTS

| | | |
|---|---|---|
| EP | 1669441 A1 | 6/2006 |
| WO | WO-1991/18087 A1 | 11/1991 |
| WO | WO-99/05989 A2 | 2/1999 |
| WO | WO-99/32171 A1 | 7/1999 |
| WO | WO-00/78932 A1 | 12/2000 |
| WO | WO-03/082145 A2 | 10/2003 |

(Continued)

OTHER PUBLICATIONS

Invitation to Pay Additional Fees dated Jul. 14, 2008 in connection with PCT/US2007/081142.

(Continued)

*Primary Examiner* — Blaine Lankford
(74) *Attorney, Agent, or Firm* — Wolf, Greenfield & Sacks, P.C.

(57) ABSTRACT

Described are compositions and methods for treating liver disease, e.g., acute liver disease, using bone marrow-derived stem cells and bone marrow-derived stem cell conditioned media.

5 Claims, 23 Drawing Sheets

Specification includes a Sequence Listing.

(56) References Cited

FOREIGN PATENT DOCUMENTS

| WO | WO-03/104411 A2 | 12/2003 |
| --- | --- | --- |
| WO | WO-2004/090112 A2 | 10/2004 |
| WO | WO-2005/107928 A2 | 11/2005 |
| WO | WO-2006/050091 A2 | 5/2006 |
| WO | WO-2006/121445 A2 | 11/2006 |

OTHER PUBLICATIONS

International Search Report and Written Opinion dated Sep. 30, 2008 in connection with PCT/US07/081142.
International Preliminary Report on Patentability dated Apr. 23, 2009 in connection with PCT/US2007/081142.
Extended European Search Report dated Mar. 8, 2010 in connection with EP 07868423.0.
Extended European Search Report dated Mar. 26, 2013 in connection with EP 12176014.4.
Abdel-Aziz et al., "Reversibility of hepatic fibrosis in experimentally induced cholestasis in rat," Am. J. Pathol., 137:1333-1342 (1990).
Arkadopoulos et al., "Liver assist systems: state of the art," Intl. J. Artif. Organs, 21:781-787 (1998).
Fang et al., "Systemic infusion of FLK1(+) mesenchymal stem cells ameliorate carbon tetrachloride-induced liver fibrosis in mice," Transplantation, 78(1):83-88 (2004).
Hiratsuka et al., Three novel single nucleotide polymorphisms (SNPs) of the CYP2B6 gene in Japanese individuals. Drug Metab Pharmacokinet. Apr. 2004;19(2):155-8.
Horwitz et al., "Isolated allogeneic bone marrow-derived mesenchymal cells engraft and stimulate growth in children with osteogenesis imperfecta: Implications for cell therapy of bone," Proc. Natl. Acad. Sci. USA, 99:8932-8937 (2002).
Humes, Stem Cells: The Next Therapeutic Frontier. Trans Am Clin Climatol Assoc. 2005;116:167-84.
Iredale et al., "Mechanisms of Spontaneous Resolution of Rat Liver Fibrosis," J. Clin. Invest., 102:538-549 (1998).
Isoda et al., Maintenance of hepatocyte functions by coculture with bone marrow stromal cells. J . Biosci Bioeng. 2004;97(5):343-6.
Lee et al., In vitro hepatic differentiation of human mesenchymal stem cells. Hepatology. Dec. 2004;40(6):1275-84.
Parekkadan et al., Immunomodulation of activated hepatic stellate cells by mesenchymal stem cells. Biochem Biophys Res Commun. Nov. 16, 2007;363(2):247-52. Epub May 30, 2007.
Parekkadan et al., Mesenchymal stem cell-derived molecules reverse fulminant hepatic failure. PLoS One. Sep. 26, 2007;2(9):e941.
Parekkadan, Bone Marrow Stromal Cell-Derived Immunotherapeutics. Presentation. Adult Mesenchymal Stem Cells in Regenerative Medicine Conference. Cleveland, OH. Aug. 2007. 6 pages.
Pittenger et al., "Mesenchymal stem cells and their potential as cardiac therapeutics," Circ. Res., 95:9-20 (2004).
Pittenger et al., "Multilineage potential of adult human mesenchymal stem cells," Science, 284:143-147 (1999).
Qihao et al., "Spheroid Formation and Differentiation into Hepatocyte-Like Cells of Rat Mesenchymal Stem Cell Induced by Co-Culture with Liver Cells," DNA and Cell Biology, 26(7):497-503 (2007).
Sakaida et al., "Transplantation of bone marrow cells reduces CC14-induced liver fibrosis in mice," Hepatology, 40:1304-1311 (2004).
Sass et al., Fulminant Hepatic Failure. Liver Transplant. 2005;11:594-605.
Shinoda et al., Treatment of fulminant hepatic failure in rats using a bioartificial liver device containing porcine hepatocytes producing interleukin-1 receptor antagonist. Tissue Eng. May 2006;12(5):1313-23.
Takeda et al., "Availability of bone Marrow Stromal Cells in Three-Dimensional Coculture with Hepatocytes and Transplantation into Liver-Damaged Mice," Journal of Bioscience and Bioengineering, 100(1):77-81 (2005).
Van Poll et al., Mesenchymal stem cell-derived molecules directly modulate hepatocellular death and regeneration in vitro and in vivo. Hepatology. May 2008;47(5):1634-43.
Yagi et al., Long-term superior performance of a stem cell/hepatocyte device for the treatment of acute liver failure. Tissue Eng Part A. Nov. 2009;15(11):3377-88.
Yagi et al., Reactive bone marrow stromal cells attenuate systemic inflammation via sTNFR1. Mol Ther. Oct. 2010;18(10):1857-64. Epub Jul. 27, 2010.
Yagi, Long-term superior performance of a stem cell/hepatocyte device for the treatment of acute liver failure. Tissue Eng Part A. Nov. 2009;15(11):3377-88.
Yarmush et al., "Assessment of artificial liver support technology," Cell Transplant, 1:323-341 (1992).
Zhao Bone marrow-derived mesenchymal stem cells protect against experimental liver fibrosis in rats. World J Gastroenterol. Jun. 14, 2005;11(22):3431-40.

FIG. 2
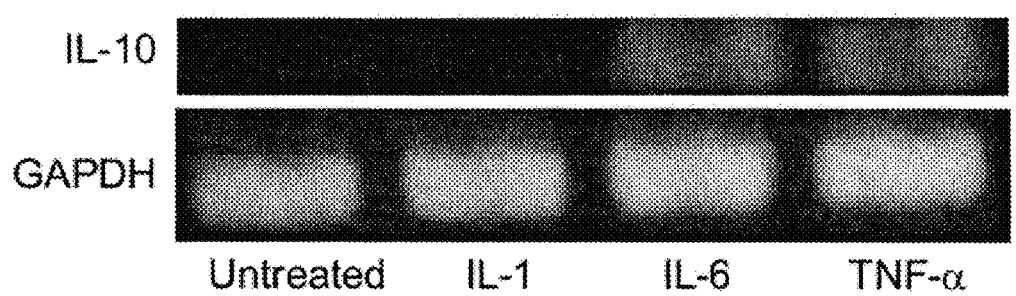
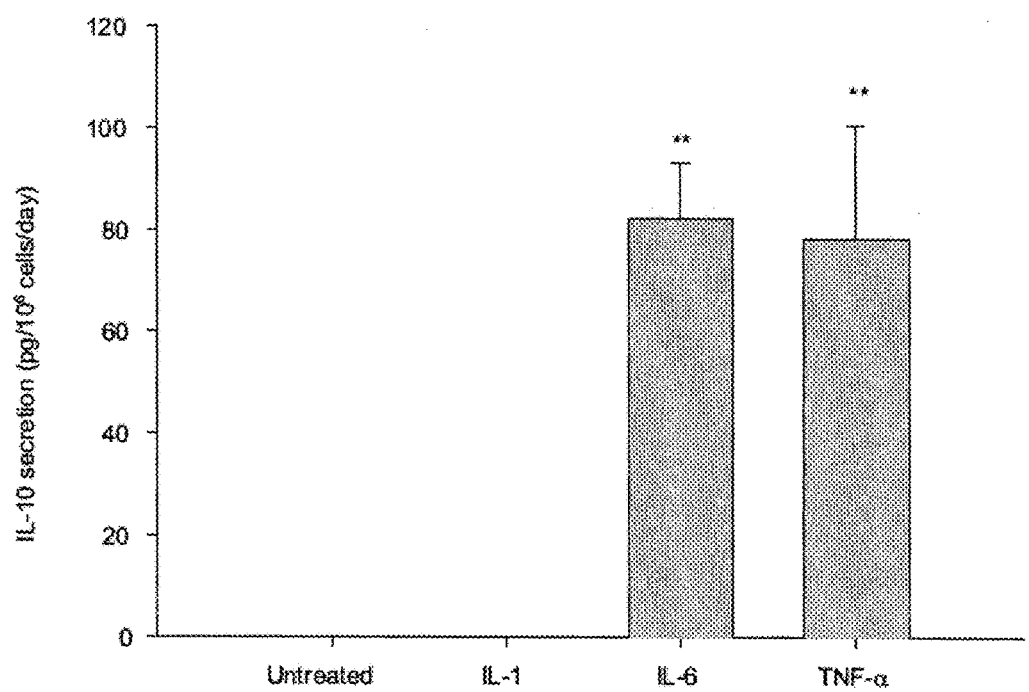
FIG. 3

FIG. 5
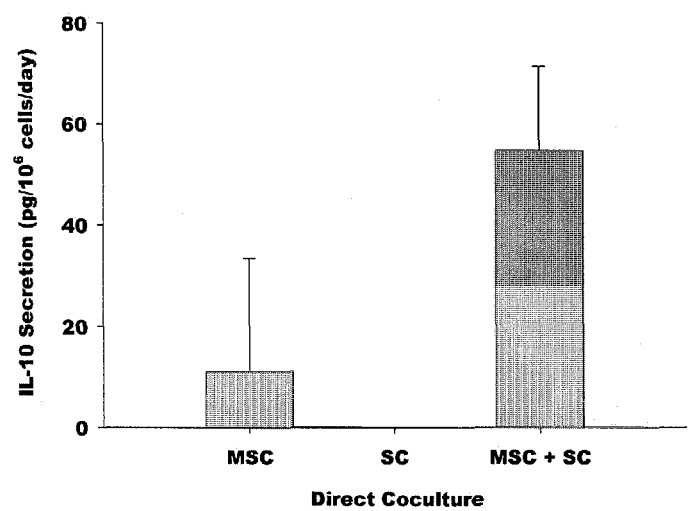
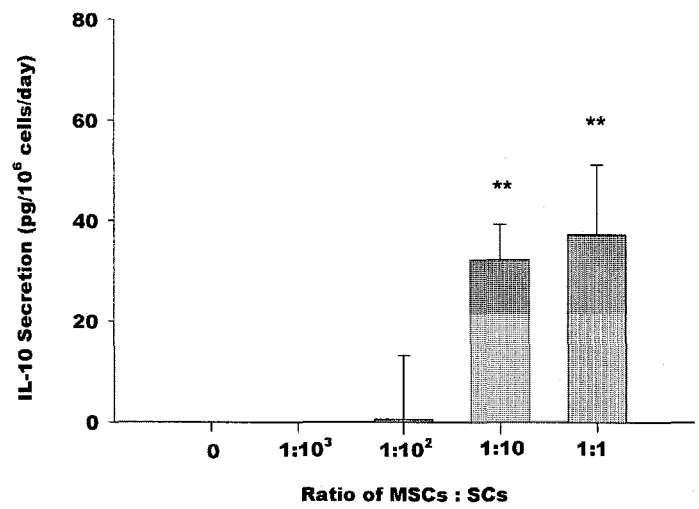
FIG. 6

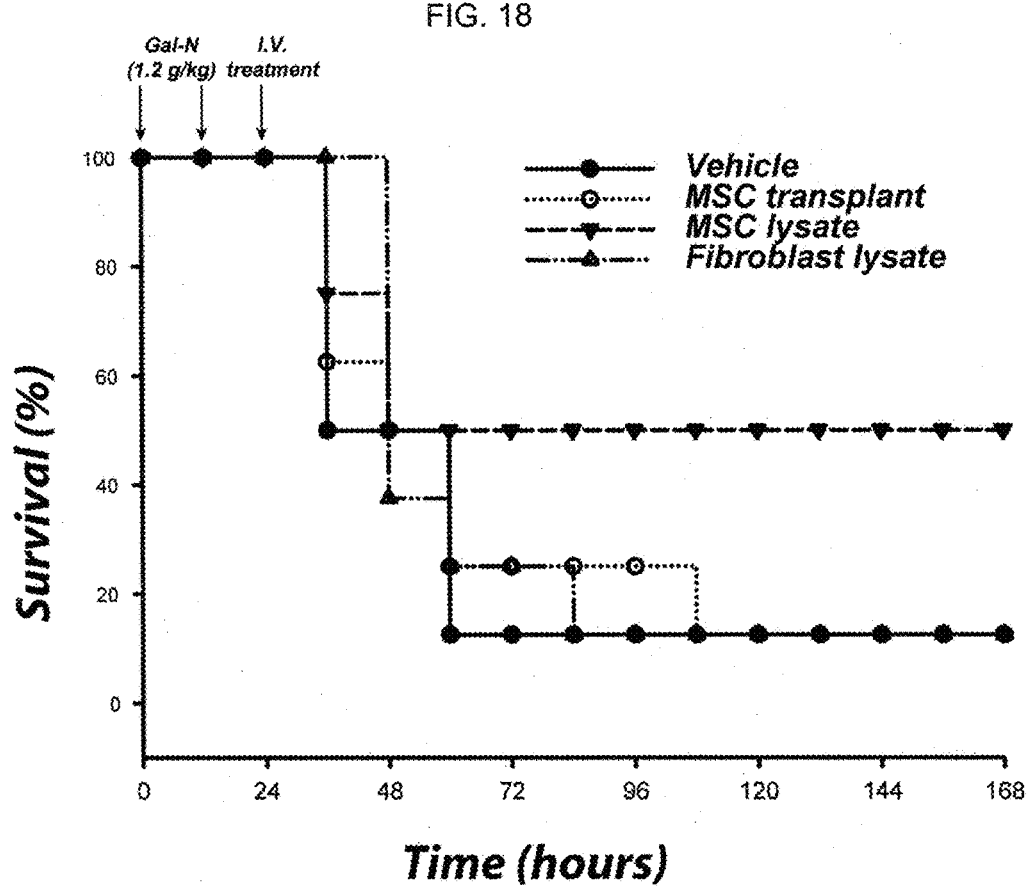

FIG. 20
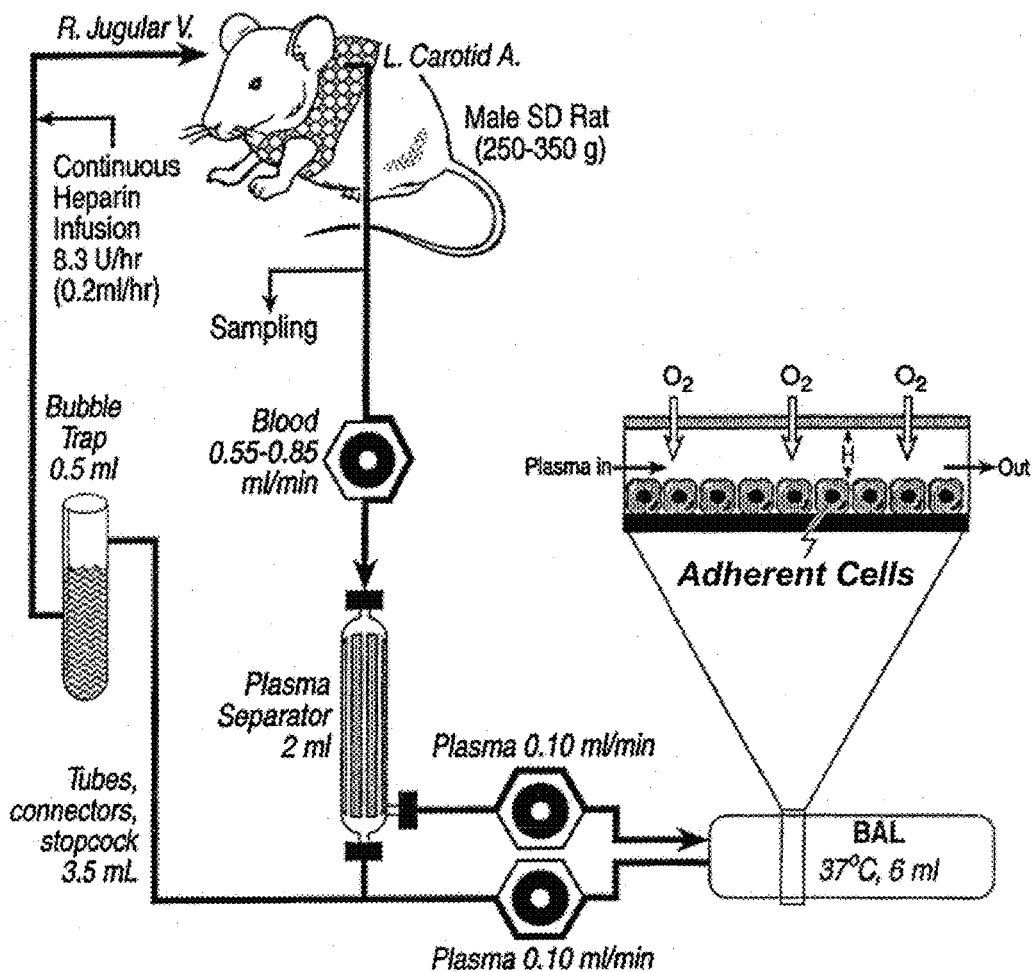
D-galactosamine Induction
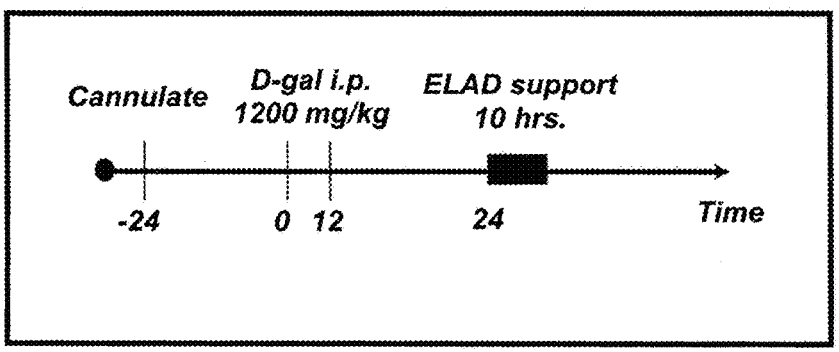

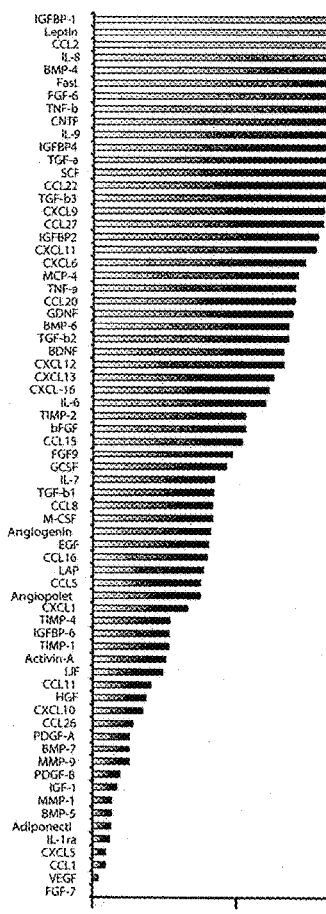
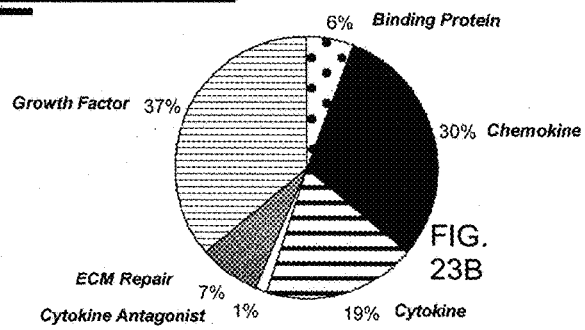
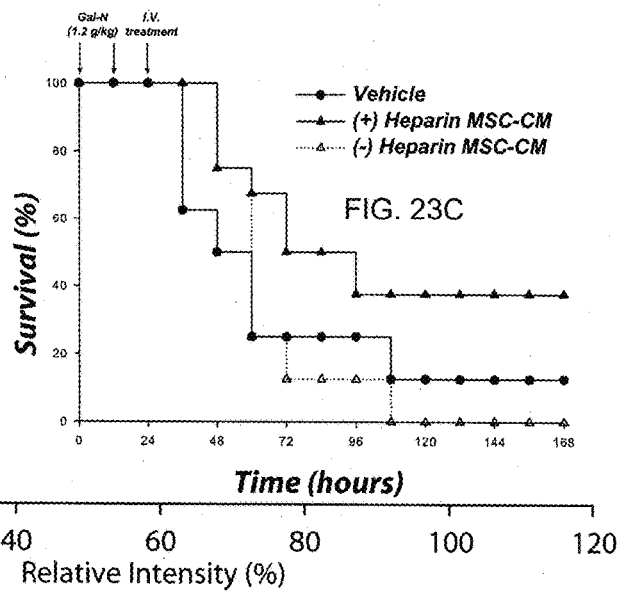
FIG. 23A
FIG. 23B
FIG. 23C

SEQUENCE LISTING

<160> NUMBER OF SEQ ID NOS: 26

<210> SEQ ID NO 1
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 1
aagcctgacc acgctttcta                    20

<210> SEQ ID NO 2
<211> LENGTH: 19
<212> TYPE: DNA
<213> ORGANISM: Artificial Sequence
<220> FEATURE:
<223> OTHER INFORMATION: synthetic polynucleotide

<400> SEQUENCE: 2

```
gtagagcggg gtttcacca                                                19

<210> SEQ ID NO 3
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 3
gagtcaacgg atttggtcgt                                               20

<210> SEQ ID NO 4
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 4
ttgattttgg agggatctcg                                               20

<210> SEQ ID NO 5
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 5
caactgggtg ctttcagaca                                               20

<210> SEQ ID NO 6
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 6
aacccatgaa gcgatggtag                                               20

<210> SEQ ID NO 7
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 7
gtctttgtct ccgccgtaag                                               20

<210> SEQ ID NO 8
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 8
ctgaacttct ggagccttcg                                               20

<210> SEQ ID NO 9
<211> LENGTH: 20
<212> TYPE: DNA
<213> ORGANISM: Artificial Sequence
```

```
<220> FEATURE:
<223> OTHER INFORMATION: synthetic polynucleotide

<400> SEQUENCE: 9
gcaagttctg cctgttcctc                                              20

<210> SEQ ID NO 10
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 10
gcactgaacc aacccacttt                                              20

<210> SEQ ID NO 11
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 11
cgagctatcg cggtaaagac                                              20

<210> SEQ ID NO 12
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 12
tgtagctttc accgttgcag                                              20

<210> SEQ ID NO 13
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 13
actcccagaa aagcaagcaa                                              20

<210> SEQ ID NO 14
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 14
cgagcaggaa tgagaagagg                                              20

<210> SEQ ID NO 15
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 15
acaccgaagg tggctatgtc                                              20
```

```
<210> SEQ ID NO 16
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 16
tagagtcagg gcaaggcagt                                               20

<210> SEQ ID NO 17
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 17
ccggagagga gacttcacag                                               20

<210> SEQ ID NO 18
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 18
cagaattgcc attgcacaac                                               20

<210> SEQ ID NO 19
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 19
caaaactggt ggcgaatctt                                               20

<210> SEQ ID NO 20
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 20
gccacgaggt catccactat                                               20

<210> SEQ ID NO 21
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 21
gcctcctgta attgctctgc                                               20

<210> SEQ ID NO 22
<211> LENGTH: 20
<212> TYPE: DNA
<213> ORGANISM: Artificial Sequence
<220> FEATURE:
<223> OTHER INFORMATION: synthetic polynucleotide
```

-continued

```
<400> SEQUENCE: 22
gccaaaaatc ctggagcata                                          20

<210> SEQ ID NO 23
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 23
tgtacacccc agcctctttc                                          20

<210> SEQ ID NO 24
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 24
cttctcgcca agacctcaac                                          20

<210> SEQ ID NO 25
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 25
atgacatcaa gaaggtggtg                                          20

<210> SEQ ID NO 26
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 26
cataccagga aatgagcttg                                          20
```

COMPOSITIONS, METHODS, AND DEVICES FOR TREATING DISEASE

CLAIM OF PRIORITY

This application is a continuation of U.S. patent application Ser. No. 13/460,315 filed Apr. 30, 2012, which is a continuation of U.S. patent application Ser. No. 11/871,071 filed Oct. 11, 2007, which claims the benefit under 35 USC § 119(e) of U.S. Provisional Patent Application No. 60/850,778 filed on Oct. 11, 2006, U.S. Provisional Patent Application No. 60/851,234 filed on Oct. 12, 2006, U.S. Provisional Patent Application No. 60/923,138 filed on Apr. 12, 2007, and U.S. Provisional Patent Application No. 60/995,316 filed Sep. 26, 2007. The entire contents of all of the foregoing applications are hereby incorporated by reference herein.

FEDERALLY SPONSORED RESEARCH OR DEVELOPMENT

This invention was made with Government support under Grant Nos. R01 DK43371, K18 DK076819, and K08 DK66040 awarded by the National Institutes of Health. The Government has certain rights in the invention.

TECHNICAL FIELD

This invention relates to compositions and methods for treating diseases and disorders related to degeneration of the liver.

BACKGROUND

Liver failure is the inability of the liver to perform its normal synthetic and metabolic function as part of normal physiology. Acute liver failure can occur in as little as 48 hours, and typically coincides with the loss or dysfunction of 80-90% of liver cells. Liver failure is a life-threatening condition that demands urgent medical care.

Acute liver failure has an estimated prevalence of 2000 cases per year and a mortality rate of approximately 80 percent.

In many cases, orthotopic liver transplantation is the only effective treatment for acute liver failure. The use of such transplants, however, is limited due to donor shortages, high cost, and the requirement for life-long immunosuppression. Thus, there is a clear need for alternative treatments for the treatment of liver failure.

SUMMARY

The present invention is based, at least in part, on the surprising discovery that multipotent stromal cell (MSC)-based therapy provides trophic support to the injured liver. Thus, administration of MSC conditioned media (MSC-CM), or the use of a bioartificial liver device (BAL) with MSCs, can be used to treat subjects with liver disease.

In one aspect, the present invention features methods of preparing a pharmaceutical composition for the treatment of liver disease. In some embodiments, the methods include providing a population of undifferentiated multipotent stromal cells (MSCs), culturing the undifferentiated MSCs in a medium, e.g., at about 80% confluency, e.g., using about $1\times10^2$ cells/cm$^2$ to $1\times10^4$ cells/cm$^2$, e.g., for a time sufficient for a desired amount of active factors to be produced, e.g., 6, 12, 18, 24, 36, or 48 hours, e.g., 12-48 hours, 12-36 hours, 24-36 hours, e.g., 24 hours, obtaining the medium (MSC-conditioned medium (MSC-CM)), fractionating the medium using known fractionation methods, e.g., by one or more of (1) charge, (2) size, and/or (3) heparin sulfate binding, selecting a fraction of the medium that is capable of one or both of promoting hepatocyte proliferation and/or inhibiting hepatocyte death, and optionally, formulating the selected fraction for administration to a mammal, e.g., for systemic administration, e.g., by intravenous administration. Preferably, the MSCs are maintained in culture in an undifferentiated state. In general, the MSC-CM and active fractions thereof will be cell-free. In some embodiments, the composition is concentrated 25-fold. In some embodiments, the composition includes a serum free tissue culture medium or PBS. In some aspects, the methods include lyophilizing the composition.

In another aspect, the present invention features pharmaceutical compositions including MSC-CM or an active fraction thereof, e.g., produced by a method described herein.

In a further aspect, the present invention features extracorporeal liver support devices. In some embodiments, the devices include a purified population of undifferentiated MSCs. In some embodiments, the devices also include a population of primary hepatocytes. Thus, the invention provides systems for treating blood or plasma from a mammal. The systems include an extracorporeal bioreactor (EB) including a fluid treatment compartment and a cell compartment, and a selectively permeable barrier separating the fluid treatment compartment and the cell compartment, wherein the cell compartment comprises a population of undifferentiated multipotent stromal cells (MSCs). In addition to the MSCs, the cell compartment can also include a population of primary hepatocytes. The selectively permeable barrier can be, for example, a bundle of hollow fibers, or a flat membrane; suitable barriers are known in the art.

In general, the EB also includes a biological fluid inlet and a biological fluid outlet, wherein the biological fluid inlet and outlet permit fluid communication between the fluid treatment compartment and a bloodstream of the mammal.

The systems will preferably also include one or a plurality of pumps for circulating the blood or plasma, e.g., from the subject through the fluid treatment compartment of the EB and back to the subject.

The systems can also include an ultrafiltration cartridge in fluid communication with the subject and/or fluid treatment compartment, such that blood from the subject is separated into ultrafiltrate/plasma and cellular components, and the UF/plasma is circulated through the fluid treatment compartment of the EB while the cellular components of the blood are returned to the subject.

The systems described herein can be used in methods of treating liver disease in a subject. The methods include identifying a subject having a liver disease; providing a system for treating blood or plasma from a mammal that includes an extracorporeal bioreactor (EB) including a fluid treatment compartment and a cell compartment, and a selectively permeable barrier separating the fluid treatment compartment and the cell compartment, wherein the cell compartment includes a population of undifferentiated multipotent stromal cells (MSCs) (and optionally a population of primary hepatocytes); and exposing the subject's plasma or blood to the MSCs in the EB.

The systems can also be used in methods for treating blood or plasma from a subject having a liver disease. The methods include identifying a subject having a liver disease; providing a system as described herein; removing blood or plasma from the subject; introducing the blood or plasma into the fluid treatment compartment of the EB; and allowing the blood or plasma to flow through and exit the fluid treatment compartment, thereby treating the blood or plasma.

In an additional aspect, the present invention provides methods of treating liver disease in a subject. In some embodiments, these methods include identifying a subject in need of treatment, and administering to the subject an effective amount of a pharmaceutical composition including MSC-CM or an active fraction thereof, e.g., produced by a method described herein. The subject can be identified, for example, by evaluating the level of a serum marker of liver function. The methods can include selecting a subject on the basis that they have a liver disease, e.g., as determined by evaluating the level of a serum marker of liver function.

A number of serum markers of liver function are known in the art, including, but not limited to, lactate dehydrogenase (LDH), alkaline phosphatase (ALP), aspartate aminotransferase (AST), alanine aminotransferase (ALT), serum bilirubin, albumin and/or globulins.

In certain embodiments, treatment continues until the subject's level of a serum marker of liver function is within the normal range as determined by the subject's clinician, e.g., for a time sufficient to ameliorate a symptom or improve a clinical parameter of the liver disease, e.g., a time selected by a clinician or health care provider. In some embodiments, the liver disease to be treated is acute liver failure. In some embodiments, the acute liver failure is fulminant hepatic failure. In some embodiments, the liver disease to be treated is liver fibrosis. In some aspects, the composition is administered using an intravenous bolus technique.

In yet another aspect, the present invention provides additional methods for treating liver disease in a subject. These methods include identifying a subject in need of the treatment, providing a system including an extracorporeal bioreactor (EB) including a purified population of undifferentiated multipotent stromal cells (MSCs), and exposing the subject's plasma or blood to the MSCs in the EB. In some embodiments, treatment can continue for a time sufficient to ameliorate a symptom or improve a clinical parameter of the liver disease, e.g., a time selected by a clinician or health care provider. In some embodiments, the subject is identified by evaluating the level of a serum marker of liver function, e.g., lactate dehydrogenase (LDH), alkaline phosphatase (ALP), aspartate aminotransferase (AST), alanine aminotransferase (ALT), serum bilirubin, albumin, and/or globulins. In some embodiments, the liver support device also includes a purified population of primary hepatocytes.

In another aspect, the present invention provides methods for identifying a biologically active component for the treatment of a liver disease, by (i) obtaining a sample of a medium containing factors secreted from a purified undifferentiated multipotent stromal cell population (MSC), (ii) obtaining a fraction of the medium using fractionation methods known in the art, (iii) assaying the ability of the fraction to promote hepatocyte proliferation or inhibit hepatocyte death, e.g., in vitro or in vivo, (iv) selecting a fraction of the medium that is capable of promoting hepatocyte proliferation or inhibiting hepatocyte death, (v) optionally repeating the steps of (i) to (iv), and (vi) identifying one or more molecules present in the selected fraction. In some embodiments, distinct fractions are obtained according to one or both of size or charge. In some embodiments, the sample of the medium is a heparin sulfate binding fraction of the medium.

The term "acute liver failure" includes, but is not limited to, the conditions referred to by the terms hyperacute liver failure, acute liver failure, subacute liver failure, and fulminant hepatic failure (FHF).

To "treat" means to reduce one or more symptoms of liver disease, e.g., to promote an improvement in liver function as evaluated using one or more serum markers of liver function (e.g., lactate dehydrogenase (LDH), alkaline phosphatase (ALP), aspartate aminotransferase (AST), alanine aminotransferase (ALT), serum bilirubin, albumin and globulins), and, thus, to ameliorate at least one symptom, e.g., a symptom associated with parenchymal cell loss in an organ, for example, the liver.

An "effective amount" is an amount sufficient to produce a beneficial or desired result. For example, a therapeutically effective amount is one that achieves a desired therapeutic effect, e.g., to ameliorate a symptom or improve a clinical parameter of a disease, e.g., a liver disease. This amount can be the same or different from a prophylactically effective amount, which is an amount necessary to prevent onset of disease or disease symptoms.

An "active fraction" is a fraction that can promote hepatocyte proliferation or inhibit hepatocyte death, e.g., in a culture of primary hepatocytes.

As used herein, the terms "patient," "subject," and "individual" are used interchangeably to refer to a mammal, including, without limitation, humans, farm animals, sport animals, pets, primates, horses, dogs, cats, rats, and mice. In some embodiments, the subject is a non-human mammal, e.g., an experimental animal or veterinary subject.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 2 is an image of a representative RT-PCR agarose gel showing IL-10 mRNA expression levels. GAPDH served as an internal control for RT-PCR analysis.

FIG. 3 is a bar graph showing mean ELISA results from two independent experiments, each of which was performed in triplicate. Error bars are standard deviation. **$p<0.01$ compared to unstimulated MSCs.

FIG. 5 is a bar graph showing ELISA measurement of IL-10 secretion after 2 days of monoculture or 1:1 direct co-culture of MSCs and SCs.

FIG. 6 is a bar graph showing IL-10 secretion as a function of MSC number after 4 days of 1:1 indirect co-culture with activated SCs, determined by RT-PCR. Results are the mean of two independent experiments performed in triplicate. Error bars are standard deviation. $**p<0.01$ compared to SCs alone (MSC:SC=0).

FIG. 18 is a line graph showing the results of Kaplan-Meier survival analysis of Gal-N administered rats treated with cell transplants or lysates. Time points of interventions are stated above survival plots. Results are cumulative data of two independent experiments (N=8 per each group) using different batches of MSCs. P-value determined by Log Rank Test.

FIG. 20 is a schematic representation of an exemplary extracorporeal circuit. Briefly, circuits were primed with sterile, heparinized Sprague-Dawley rat plasma, which was filtered immediately before use. The rat was administered 100 U heparin (0.1 ml) systemically through the venous line 5 minutes before the start of perfusion. The arterial and venous lines were subsequently connected to the extracorporeal circuit. Arterial blood was pumped at 0.55-0.85 ml/minute through #13 MASTERFLEX silicone tubing (Cole-Palmer Instrument Co.) by a digital variable-speed peristaltic pump (Cole-Palmer Instrument Co.) drive. A plasma separator (MICROKROS, membrane material: mixed esters of cellulose, membrane pore size: 0.2 um, membrane surface area: 16 cm$^2$; Spectrum Laboratories Inc., Laguna Hills, Calif.) was placed after the pump. Separated plasma was pumped though the BAL by means of second and third peristaltic pump at a flow rate of 0.1 ml/minute. The separated plasma and remaining blood components were reunited before entering a bubble trap. Reconstituted blood returned to the animal through the venous cannula. During perfusion, the heparin (41.5 U/mL) with 5% dextrose solution was administered continuously through the venous line at a rate of 0.2 ml/hour via a syringe infusion pump. In this configuration, the dead volume of the entire perfusion system was 12 ml, of which, 6 ml were accounted for by the BAL. Oxygenating gas (21% $O_2$, 5% $CO_2$, 74% $N_2$) flow was established through the chamber above the internal membrane of the BAL.

FIG. 23A-C shows that MSC-CM is composed of high levels of chemokines that correlate with survival benefit seen in FHF. Serum-free MSC-CM was analyzed using an antibody array for 174 specified proteins. FIG. 23A is a bar graphs showing the results o densitometry analysis of spotted antibody array results. Data are presented as spot intensity relative to the negative control and normalized to positive control. FIG. 23B is a pie chart showing cluster analysis of MSC secreted proteins based on reported function. MSC-CM was fractionated over a heparin-agarose column into heparin bound and unbound fractions. FIG. 23C is a line graph showing the results of Kaplan-Meier survival analysis of Gal-N administered rats treated with the (+) heparin MSC-CM and (−) heparin MSC-CM. Time points of interventions are stated above survival plots. Results for (C) are cumulative data of two independent experiments using different batches of MSC-CM (N=8 per each group). P-value determined by Log Rank Test.

DETAILED DESCRIPTION

Figure 1:
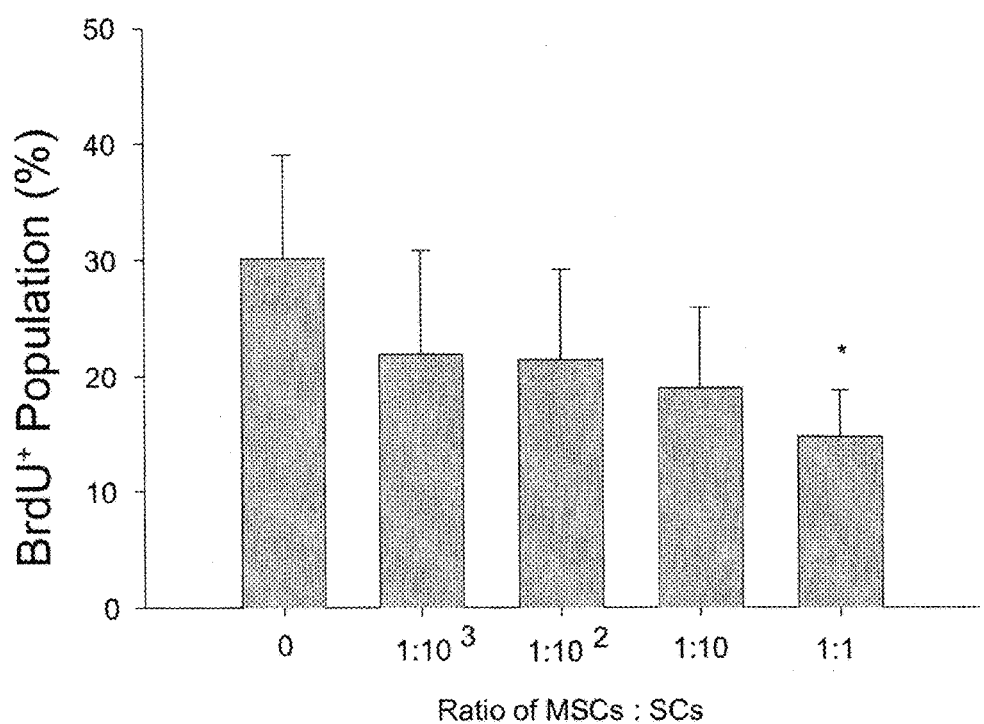
FIG. 1 is a bar graph showing Bromodeoxyuridine (5-bromo-2-deoxyuridine, BrdU) incorporation in activated SCs as a function of MSC:SC ratio. Proliferation of activated SCs is inhibited by indirect co-culture with MSCs. Data represent the mean of two experiments performed in triplicate. Error bars are standard deviation. *$p<0.05$ compared to SCs alone (MSC:SC=0).

The present invention is based, at least in part, on the surprising discovery that multipotent stromal cells (MSCs), and agents secreted therefrom, provide trophic support to the injured liver. Without wishing to be bound by theory, it is believed that this therapeutic effect is a result of inhibiting hepatocellular death and stimulating hepatocellular regeneration. Thus, methods of treatment that include parenteral administration of a cell-free MSC-conditioned media composition, or the use of artificial liver devices including MSCs, can be used to treat subjects with liver disease, as described herein.

At least in part, the data presented herein demonstrate that MSCs, and agents secreted therefrom, are capable of modulating the function of activated stellate cells via paracrine mechanisms, treating an inflammatory condition, and providing trophic support to the injured liver by inhibiting hepatocellular death and stimulating hepatocyte regeneration. Accordingly, MSC-based therapy, as described herein, is useful in the treatment of any acute and/or chronic condition, including autoimmune and inflammatory conditions, in which the inhibition of cell death and stimulation of tissue repair would be beneficial. Such conditions include, but are not limited to, for example, liver disease (e.g., fibrosis, cirrhosis, acute liver failure, fulminant hepatic failure (FHF), and any other degenerative liver disease), ischemic injury (e.g., myocardial infarction and stroke), kidney failure, acute pancreatitis, and autoimmune disease. MSC based therapy may also be beneficial in any condition or disorder in which the action of trophic secreted molecules are beneficial.

MSC Therapy

As described herein, MSCs and agents secreted therefrom, e.g., in an MSC conditioned media composition, can be used to treat liver diseases or disorders involving the loss or damage of parenchymal liver cells in a subject. In general, the etiology of these diseases or disorders can be a local or systemic inflammatory response. However, other liver diseases or disorders associated with the loss or damage of parenchymal liver cells are also included.

As described herein, MSCs and agents secreted therefrom, e.g., in an MSC conditioned media composition, are particularly useful in the treatment of acute liver failure in a subject, for example, FHF. In some embodiments, a subject will be selected for treatment using the compositions and methods described herein based on a positive diagnosis of liver disease. Liver disease can be diagnosed using methods known in the art, for example, using one or more of the liver function assays described herein, or based on the judgment of a clinician.

In some embodiments, treatment is performed using administration of a MSC conditioned medium (MSC-CM) composition, or an active fraction thereof. In some embodiments, treatment is performed using a MSC-based extracorporeal bioreactor (MSC-EB).

MSC Isolation

Multipotent stromal cells (MSCs) are also referred to in the art as bone marrow-, adipose-, umbilical cord-, and placental-derived mesenchymal stem cells, and bone marrow-, adipose-, umbilical cord-, and placental-derived stromal cells. MSCs can be isolated using methods known in the art, e.g., from bone marrow mononuclear cells, umbilical cord blood, adipose tissue, placental tissue, based on their adherence to tissue culture plastic. For example, MSCs can be isolated from commercially available bone marrow aspirates (see Example 1). Purification of MSCs can be achieved using methods known in the art, e.g., the methods described herein, including but not limited to FACS.

In some embodiments, an MSC preparation will include a solution. This solution can contain those components required to support MSC survival and growth. Such components are routinely present in commercially available tissue culture media, for example, Dulbecco's modified Eagle's medium (DMEM). Such components include, for example, amino acids, vitamins, a carbon source (natural and non-natural), salts, sugars, plant derived hydrolysates, sodium pyruvate, surfactants, ammonia, lipids, hormones or growth factors, buffers, non-natural amino acids, sugar precursors, indicators, nucleosides and/or nucleotides, butyrate or organics, DMSO, animal derived products, gene inducers, non-natural sugars, regulators of intracellular pH, betaine or osmoprotectant, trace elements, minerals, non-natural vitamins. Additional components that can be used to supplement a commercially available tissue culture medium include, for example, animal serum (e.g., fetal bovine serum (FBS), fetal calf serum (FCS), horse serum (HS)), antibiotics (e.g., including but not limited to, penicillin, streptomycin, neomycin sulfate, amphotericin B, blasticidin, chloramphenicol, amoxicillin, bacitracin, bleomycin, cephalosporin, chlortetracycline, zeocin, and puromycin), and glutamine (e.g., L-glutamine). MSC survival and growth also depends on the maintenance of an appropriate aerobic environment, pH, and temperature. In some embodiments, the solution will not include animal serum, e.g., when the MSCs are placed into a bioartificial liver device.

In some embodiments, an MSC preparation will be essentially free of non-MSC cells or cellular material. In some embodiments, an MSC preparation will contain at least 80% MSCs identified by the criteria described herein, e.g., at least 85%, 90%, 95%, 98%, 99% and above MSCs. In some embodiments, the cells in an MSC preparation will be 100% MSCs. A population of cells that is at least 80% MSCs can be termed a "purified" population of MSCs. In general, the methods, compositions, and devices described herein will use purified populations of MSCs.

As one example, MSCs can be cultured using Dulbecco's modified Eagle's medium supplemented with 10% fetal calf serum, 100 U/ml penicillin, 100 µg/ml streptomycin, 0.1 mM non-essential amino acids and 1 ng/ml of basic fibroblast growth factor (Life Technologies, Rockville, Md.). After 4 days of culture, non-adherent hematopoietic cells can be removed by washing with PBS. Monolayers of adherent MSCs are then cultured with medium changes 2-3 times per week. MSCs can be passaged using 0.25% trypsin/0.1% EDTA. MSCs can be routinely subcultured at a density of $5 \times 10^3$ cells/cm$^2$. MSCs can be maintained using methods known in the art (see, e.g., Pittenger et al., Science, 284: 143-147, 1999).

In some embodiments, MSCs can be used according to the methods described herein during passages 1-7, e.g., during passages 4-7, where passage one is the first passage following isolation. In general, MSCs in culture should not be allowed to exceed a cell density great than 80% confluency. Confluency can be estimated visually, for example, using a standard light microscope. Alternatively, cell confluency can be determined by performing cell counts using, for example, a standard haemocytometer. In some embodiments, 80% confluence corresponds to about $1 \times 10^6$ MSCs per 175 cm$^2$ tissue culture grade flask. In some embodiments, 80% confluence corresponds to about $5 \times 10^3$ cells/cm$^2$.

In general, it will be desirable to maintain the MSCs in an undifferentiated state. MSC differentiation status can be evaluated using methods known in the art, e.g., the MSC characterization methods described herein.

MSC Characterization

An MSC preparation (i.e., an undifferentiated MSC preparation) can be characterized prior to therapeutic use to confirm the identity, purity, and differentiation status of the cells.

MSCs display a unique and easily identifiable fibroblastoid morphology and express a unique array of antigens that react with SH2 (CD105) and SH3 (CD73) monoclonal antibodies. MSCs also have a unique ability to reproducibly give rise to adipocytes, osteoblasts, and chondrocytes in vitro (Pittenger et al., Science, 284:143-147, 1999).

As described herein, an MSC preparation (e.g., an undifferentiated MSC preparation) can be characterized by performing one or more of the following tests, which can be performed in vivo or in vitro (see Example 2):

(1) evaluating the ability of an MSC or an MSC preparation to differentiate into adipocytes, osteoblasts, and chondrocytes. Undifferentiated MSCs can give rise to all of these cell types.

(2) detecting the presence or absence of one or more of the following cell surface markers: CD29, CD44, CD73, CD90, CD105, CD106, CD11b, CD14, CD18, CD34, CD36, and CD45 on an isolated MSC or in an MSC preparation, e.g., using an array. Undifferentiated MSCs express CD105, CD106, and CD44 and do not express CD14, CD34, and CD45.

In general, positive identification of an MSC preparation (e.g., an undifferentiated MSC preparation) requires that at least 80%, e.g., at least 85%, 90%, 95%, 98%, 99% and above, or 100% of the cells in the preparation test positive for cell surface expression of CD105, CD106, and CD44 and test negative for cell surface expression of CD14, CD34, and CD45 (i.e., CD105+; CD106+; CD44+; CD14−; CD34−; CD44−).

In some embodiments, positive identification of an undifferentiated MSC preparation requires only one of the two above described tests to be performed. However, both tests can be performed.

In some embodiments, additional tests can be performed, e.g., prior to therapeutic use of an MSC preparation to confirm the absence of contaminants including, for example, bacteria, viruses, fungus, infectious proteins, and unwanted immunological molecules. Such tests are known in the art.

MSC-Conditioned Media (MSC-CM)

An MSC-CM composition can be prepared using a population of undifferentiated MSCs between passages 4-7, where passage one is the first passage following isolation. As described herein, an MSC-CM composition can be prepared using about $1 \times 10^5$ to $1 \times 10^7$ cells, e.g., about $1 \times 10^5$ to $1 \times 10^6$ cells, $1 \times 10^6$ to $1 \times 10^7$ cells, $1 \times 10^6$ to $9 \times 10^6$ cells, $1 \times 10^6$ to $8 \times 10^6$ cells, $1 \times 10^6$ to $7 \times 10^6$ cells, $1 \times 10^6$ to $6 \times 10^6$ cells, $1 \times 10^6$ to $5 \times 10^6$ cells, $1 \times 10^6$ to $4 \times 10^6$ cells, $1 \times 10^6$ to $3 \times 10^6$ cells, and $1 \times 10^6$ to $2 \times 10^6$ cells. In some embodiments, an MSC-CM composition can be prepared using $2 \times 10^6$ cells.

In some embodiments, an MSC-CM composition is prepared using about $1 \times 10^2$ cells/cm$^2$ to $1 \times 10^4$ cells/cm$^2$, e.g., about $1 \times 10^2$ cells/cm$^2$ to $1 \times 10^3$ cells/cm$^2$, $1 \times 10^3$ cells/cm$^2$ to $1 \times 10^4$ cells/cm$^2$, $1 \times 10^3$ cells/cm$^2$ to $9 \times 10^3$ cells/cm$^2$, $1 \times 10^3$ cells/cm$^2$ to $8 \times 10^3$ cells/cm$^2$, $1 \times 10^3$ cells/cm$^2$ to $7 \times 10^3$ cells/cm$^2$, $1 \times 10^3$ cells/cm$^2$ to $6 \times 10^3$ cells/cm$^2$, $1 \times 10^3$ cells/cm$^2$ to $5 \times 10^3$ cells/cm$^2$, $1 \times 10^3$ cells/cm$^2$ to $4 \times 10^3$ cells/cm$^2$, $1 \times 10^3$ cells/cm$^2$ to $3 \times 10^3$ cells/cm$^2$, and $1 \times 10^3$ cells/cm$^2$ to $2 \times 10^3$ cells/cm$^2$. In some embodiments, an MSC-CM composition can be prepared using about $5 \times 10^3$ cells/cm$^2$. In some embodiments, an MSC-CM composition can be prepared using two populations of $1 \times 10^6$ MSCs per 175 cm$^2$, i.e., an MSC-CM composition can be prepared using $2 \times 10^6$ cells.

In some embodiments, an MSC-CM composition is prepared as follows (see also Example 4):

(1) Wash 70-80% confluent MSCs thoroughly with phosphate buffered saline (PBS);

(2) Culture MSCs from (1) for about 12, 24, 36, or 48 hours, e.g., 24 hours in an appropriate volume of serum free culture medium containing DMEM, or an equivalent thereof, supplemented with 0.05% bovine serum albumin (BSA) (note: media volume will vary depending on the size of the cell culture vessel) in a suitable vessel, e.g., a T175 cm$^2$ flask, with each vessel/flask at 80% confluency, equivalent to about 5×10$^3$ cells/cm$^2$; and (3) Collect MSC culture media from (2).

The collected MSC-CM composition can be concentrated, e.g., using methods known in the art, for example, ultrafiltration units with a 3 kD cutoff (AMICON Ultra-PL 3, Millipore, Bedford, Mass., USA). For example, the MSC-CM composition can be concentrated at least 2-fold to 10-fold, 10-fold to 20-fold, 20-fold to 30-fold, 30-fold to 49-fold, and above. As one example, an MSC-CM composition is concentrated 25-fold.

In some embodiments, the MSC-CM composition comprises culture medium containing DMEM supplemented with 0.05% bovine serum albumin (BSA). In some embodiments, the MSC-CM composition does not contain any animal serum. In some embodiments, the MSC-CM composition comprises PBS. Alternatively, the MSC-CM composition is provided in lyphophilized form.

In some embodiments, an MSC-CM composition can be fractionated by size or by charge. In some embodiments, for example, an MSC-CM composition can be fractionated into heparin sulfate binding and non heparin binding fractions. For example, in heparin sulfate fractionation experiments, a concentrated MSC-CM composition can be passed over a heparin column, or other columns e.g., an ion-exchange, size, reverse-phase or other chromatographic separation methods per vendor's instructions. Flow-through and eluted fractions can then be collected separately. The eluted fractions (i.e., the heparin-binding fraction) can then be collected and optionally concentrated, as described above.

In some embodiments, an MSC-CM composition is at least 50%, 60%, 70%, 80%, 90%, and 100% free of non-heparin binding material.

Methods of Treatment

The methods described herein can be used for treating liver disease in a subject. In some embodiments, the etiology of the liver disease to be treated may be a local or systemic inflammatory response. The methods described herein are of particular use for the treatment of FHF in a subject. The methods include treating a subject diagnosed as having FHF, or suspected as having FHF, for example, a subject that presents to a clinician with symptoms that are typical of FHF. In some embodiments, the methods and compositions described herein are of use in the treatment of liver fibrosis.

Generally, the methods described herein include (1) administering a therapeutically effective amount of an MSC-CM composition (or active fraction thereof) to a subject who is need of, or who has been determined to be in need of such treatment; and/or (2) treating a subject identified as in need of, or who has been determined to be in need of such treatment, with a extracorporeal liver support device or a liver assist device containing MSCs (e.g., an extracorporeal bioreactor (EB)) containing MSCs (MSC-EB).

MSC-CM Therapy

The methods described herein can include parenteral administration of a composition including one or more of (A) a purified fraction of an MSC-CM composition; (B) one or more purified fractions of an MSC-CM composition; (C) MSC-CM composition fractions of particular molecular weights, for example, 1-3 kDa, 3-6 kDa, 6-50 kDa, and 50 kDa and above, including combinations of these fractions; (D) an unfractionated MSC-CM composition; and (E) any combination of A-D. Each of these is referred to individually and collectively as the "composition" or the "MSC-CM composition." Biologically active fractions can be identified in vitro by exposing hepatocytes to apoptotic stimuli, such as actinomyosin D and TNF-α. The level of apoptosis can then be determined using, for example, TUNEL assay according to the manufacturer's instructions. Biologically active fractions will inhibit apoptosis by a statistically significant amount in this system, e.g., by 25%, 30%, 45%, 50%, 55%, 60%, 70%, 80%, 90%, or more. These in vitro observations may be complemented using in vivo assays in an acute liver failure animal model.

In some embodiments, a therapeutically effective dose of an MSC-CM composition is administered to a subject using systemic intravenous bolus injection. Bolus administration (also referred to as bolus infusion) includes administration of a dose of drug over a short period of time, e.g., by injection into a blood vessel.

In some embodiments, a therapeutically effective dose of an MSC-CM composition is administered to a subject using an intravenous drip. Other modes of administration can include any number of different routes including, but not limited to, intravenous, intradermal, subcutaneous, and percutaneous injection.

A therapeutically effective amount of an MSC-CM composition can be given to the subject in one or more administrations, applications, or dosages. The compositions can be administered from one or more times per day to one or more times per week; including once every other day. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of the compositions described herein can include a single treatment or a series of treatments.

In some embodiments, an MSC-CM composition is administered to a subject as a single daily dose or as multiple daily doses, for example, 1, 2, or 3 daily doses. Doses can be administered with or without regard to food intake.

In some embodiments, an MSC-CM composition is administered to a subject for a period of 1 to 7 days. In some embodiments, an MSC-CM composition is administered to a subject for a period of at least 1 week to 1 month, for example, at least 1, 2, 3, or 4 weeks. In a further alternative embodiment, an MSC-CM composition is administered to a subject for a period of at least 1 month to 1 year or longer. In some embodiments, an MSC-CM composition is administered until the desired therapeutic effect (e.g., functional recovery of the liver, e.g., to normal or near-normal levels, or to levels manageable by other therapeutic means) has been achieved, as decided by the subject or the subject's healthcare provider. In some embodiments, liver function can be assessed using known tests of liver function, for example, serum lactate dehydrogenase (LDH), alkaline phosphatase (ALP), aspartate aminotransferase (AST), alanine aminotransferase (ALT), bilirubin, protein levels, prothrombin time, activated clotting time (ACT), partial thromboplastin time (PTT), and prothrombin consumption time (PCT) (discussed further below).

Dosage, toxicity, and therapeutic efficacy of the composition can be determined, e.g., by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are generally preferred. While compounds that exhibit toxic side effects can be used, care should be taken to design a delivery system that targets such compounds to the site of affected tissue to minimize potential damage to uninfected cells and, thereby, reduce side effects.

In some embodiments, an MSC-CM composition can be validated and/or the therapeutic efficacy of an MSC-CM composition, e.g., of a given batch of an MSC-CM composition, can be determined using an experimental model (e.g., an animal model or an in vitro model), e.g., as described herein.

MSC-EB Therapy and Devices

The methods described herein can include the use of extracorporeal liver support devices with MSCs to treat subjects with liver disease. Such devices are also within the scope of the present disclosure.

Extracorporeal liver support devices are analogous to the devices used to perform kidney dialysis. The devices described herein are bioartificial liver (BAL) devices that include extracorporeal bioreactors (EBs), which are cartridges or vessels having at least a perfusion inlet and a perfusion outlet, and a cell compartment, e.g., a matrix, within the vessel that provides a suitable environment for living cells while allowing perfusion of the cell compartment with suitable media for maintaining the cells. Such cell compartments can be, e.g., hollow fibers, with circulation of blood or plasma outside the fibers, or flat plates; see, e.g., U.S. Pat. No. 6,759,245.

Generally, systems comprising EBs also continuously separate plasma from cellular components of blood using an ultrafiltrate generator. The ultrafiltrate (e.g., plasma) is circulated through the cartridge containing cultured cells, i.e., an EB. Alternatively, whole blood can be treated in the EB.

As noted above, EB cartridges generally contain a semipermeable barrier made of a material that allows the passage of macromolecules and other cell derived products to and from the subject's plasma. However, the cells themselves do not leave the EB. After circulation and one or multiple passes through the bioreactor, the treated ultrafiltrate (e.g., plasma) is recombined with the cellular components of the subject's blood and returned to the subject via venous access. Generally, the subject's blood or plasma is supplemented with heparin to prevent clotting. This circulation is maintained continuously for, e.g., a 10 hour support period of therapy. In current BAL systems, blood or plasma carries toxins from the patient to a bioreactor containing hepatocytes. See, e.g., Yarmush et al., Cell Transplant, 1:323 (1992), and Arkadopoulos et al., Int'l J. Artif. Organs, 21:781 (1998).

The present devices include a) a bioreactor comprising a fluid treatment compartment and a cell compartment, and optionally a selectively permeable barrier separating the fluid treatment compartment and the cell compartment; and b) a cell reservoir in fluid communication with the cell compartment of the bioreactor, wherein the cell reservoir comprises a population of undifferentiated undifferentiated multipotent stromal cells (MSCs). Blood or ultrafiltrate from a subject is passed into the fluid treatment compartment, where agents secreted by the MSCs pass into the blood or ultrafiltrate, either by direct contact between the MSCs and the blood or ultrafiltrate, or by passage of the agents across the optional selectively permeable barrier, when it is present. In the present devices and methods, MSCs in an EB are used in an undifferentiated state, as assessed using techniques described herein.

Extracorporeal liver support devices including bioreactors are also commonly referred to as bioartificial liver devices (BALs) or bioartificial liver assist devices (BLADs). A number of such devices are known in the art and can be adapted for use with MSCs. Exemplary commercially available extracorporeal liver support device that can be used as described herein include, but are not limited to, the ELAD® system currently marketed by Vital Therapies, Incorporated (shown in FIG. 1 of U.S. Pat. App. Pub. No. 2005/0182349), Circe's HEPATASSIST®, Gerlach's BELS, and Excorp Medical's BLSS. Additional suitable exemplary devices are described in U.S. Pat. Nos. 6,472,200; 5,605,835; 7,160,719; 7,273,465; 6,858,146; 6,582,955; 5,270,192; 6,759,245; and U.S. Pat. App. Pub. Nos. 2003-0017142.

Figure 25:
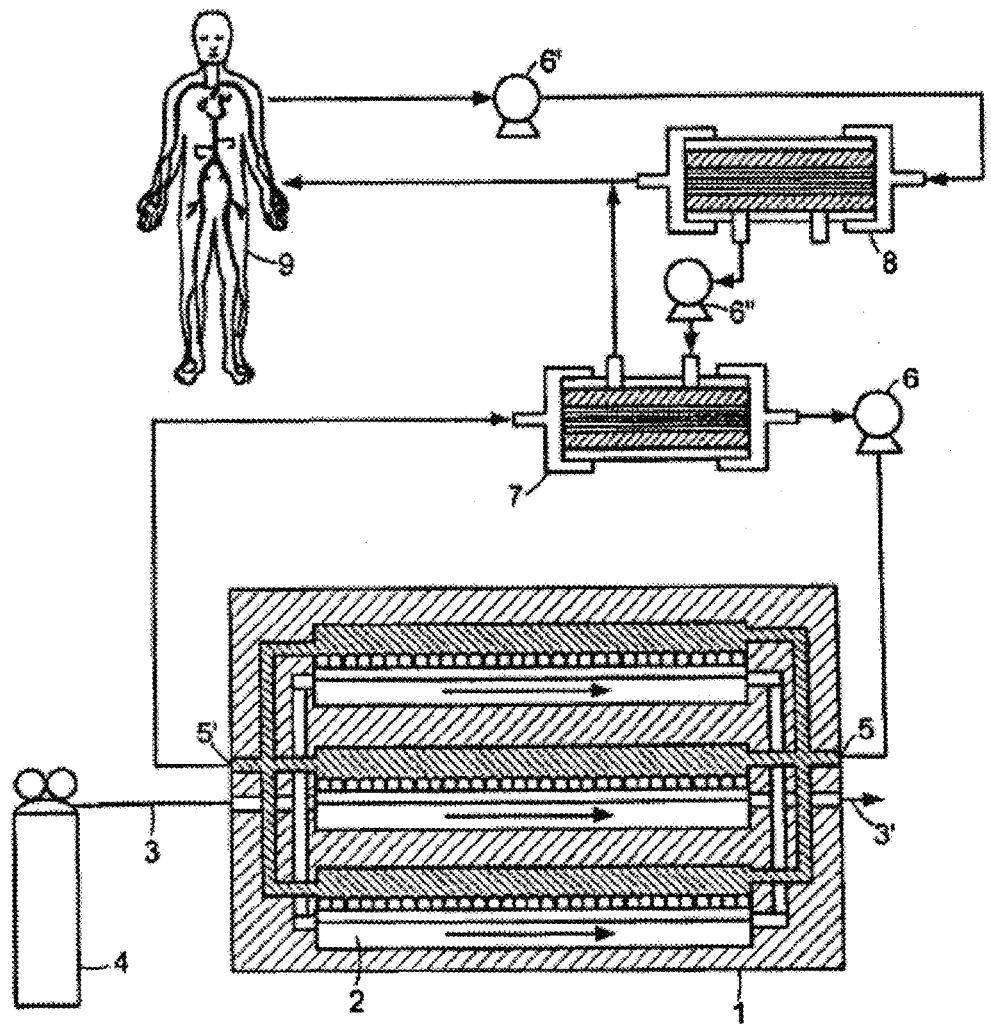
FIGS. 25 and 26 are schematic illustrations of examples of bioartificial liver systems.

FIG. 25 shows a schematic diagram of an exemplary extracorporeal liver support system in which the EBs containing MSCs as described herein can be used. The system includes an exemplary bioreactor 1 with multiple cartridges 2. The bioreactor 1 includes an oxygenated fluid inlet 3 for introducing an oxygenated fluid from an oxygenated fluid supply 4, an oxygenated fluid outlet 3', a liquid inlet 5 for introducing a biological liquid, supplied by pump 6 from immunoisolation unit 7, into the bioreactor, and a liquid outlet 5' for removing the biological liquid from the bioreactor for return to the immunoisolation unit 7. Blood from a patient 9 flows via pump 6' into a plasmapheresis unit 8, from which a portion of the plasma then flows into the immunoisolation unit 7, via pump 6". Treated plasma flows from the immunoisolation unit 7 and is mixed with blood from the plasmapheresis unit 8 prior to flowing back into the patient 9. For further details, see U.S. Pat. No. 6,759,245.

Figure 26:
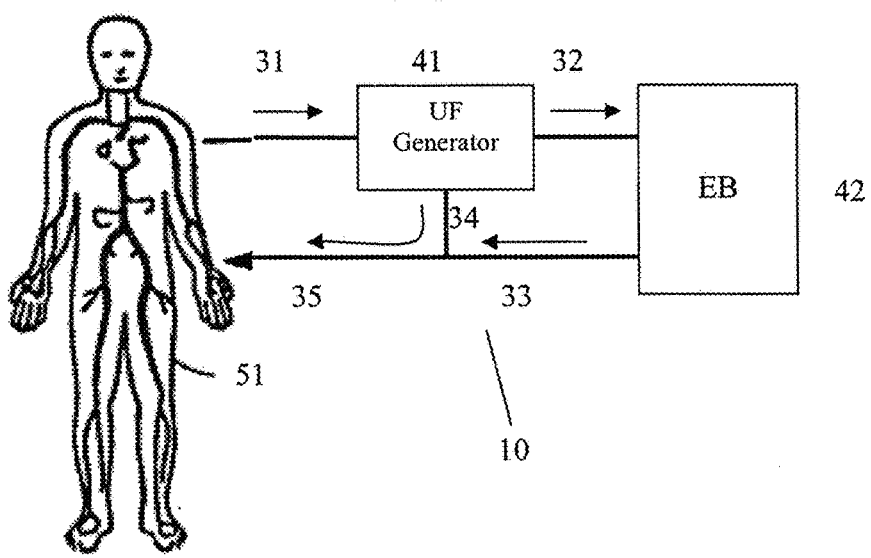

Referring to FIG. 26, another example of a bioartificial liver system is shown in schematic form (see U.S. Pat. No. 7,160,719). System 10 includes an EB 42 that includes MSCs, and optionally hepatocytes. A biological fluid to be treated (e.g., blood or plasma) can be introduced into EB 42 via biological fluid inlet pathway 32 and can exit via biological fluid outlet pathway 33. For example, a venovenous catheter can be used to place a mammal's bloodstream in fluid communication with EB 42 via biological fluid inlet path 32. In an alternative embodiment, a biological fluid can be treated in vitro using a biological fluid reservoir (not shown) in place of the mammal 51. In some embodiments, the device includes an ultrafiltrate (UF) generator 41. In those cases, blood from the mammal 51 flows along blood path 31 into UF generator 41, where the cellular components are separated from plasma. The ultrafiltered plasma then flows along path 32 into EB 42, while the cellular components rejoin the treated UF via path 34. The biological fluid then returns to mammal 51 or to the biological fluid reservoir via path 35.

Although FIGS. 25 and 26 depict the various components in a specific orientation and having similar dimensions, the components can be in any orientation, size, or shape.

In some situations, to minimize MSC differentiation, individual MSC-containing EB devices can be operated for a maximum of 24 hours. In some embodiments, MSC cells can be combined with primary hepatocytes in a conventional EB.

Thus, according to the present methods, a subject in need of therapy can be connected to a BAL device having an EB containing MSCs (MSC-EB), or containing a mixture of hepatocytes and MSCs. These methods can be used for treating blood or plasma from the subject. The method includes providing a system, as described herein, that contains an EB that includes a cell compartment containing a population of MSCs for treating the blood or plasma; removing the blood or plasma from the subject; introducing the blood or plasma into the fluid treatment compartment of the EB; and allowing the blood or plasma to flow through and exit the fluid treatment compartment, thereby treating the blood or plasma.

The flow rate of a subject's plasma through an EB can be adjusted as needed, e.g., to a rate of about 50-500 ml/minute, e.g., 50, 100, 200, 300, 400, and 500 ml/minute. In some embodiments, the flow rate will be adjusted to optimize passage of secreted agents from the undifferentiated MSCs to the ultrafiltrate. In some embodiments, the target flow rate will be 175 ml/minute. Treatment of the subject (e.g., circulation of the subject's plasma through a device) can continue for a therapeutically effective time, e.g., between 1 hour and 24 hours, e.g., about 2, 3, 4, 5, 10, 12, 15, 18, 20, or 23 hours. Subjects can undergo multiple rounds of MSC-EB therapy with each round lasting for, e.g., between 1 hour and 24 hours. MSC-EB therapy can be continued, e.g., until a desired therapeutic effect (e.g., recovery of sufficient liver function to acceptable or near-normal levels) has been achieved, as decided by the subject or the subject's healthcare provider, or until a donor liver is available for transplantation. In some embodiments, liver function can be assessed using standard tests of liver function, for example, serum LDH, ALP, AST, ALT, bilirubin, protein levels, prothrombin time, ACT, PTT, and PCT. In some embodiments, tests of liver function are performed prior to and/or following MSC-EB therapy, to assess the effectiveness of the MSC-EB therapy. Such assessments can also be made before and/or after each round of MSC-EB therapy, as well as before therapy begins and after therapy has been completed due to the desired therapeutic effect being achieved or the procurement of a donor organ.

Extracorporeal liver support devices including bioreactors are also commonly referred to as bioartificial liver devices (BALs) or bioartificial liver assist devices (BLADs). A number of such devices are known in the art and can be adapted for use with MSCs. Exemplary commercially available extracorporeal liver support device that can be used as described herein include, but are not limited to, the ELAD® system currently marketed by Vital Therapies, Incorporated (shown in FIG. 1 of U.S. Pat. App. Pub. No. 2005/0182349), Circe's HEPATASSIST®, Gerlach's BELS, and Excorp Medical's BLSS. Additional suitable exemplary devices are described in U.S. Pat. Nos. 6,472,200, 5,605,835; 7,160,719; 7,273,465; 6,858,146; 6,582,955; 5,270,192; 6,759,245; and U.S. Pat. App. Pub. Nos. 2003-0017142.

Subject Selection

The methods described herein are of particular use for the treatment of liver disease (e.g., acute liver failure) in a subject in need thereof. The methods include: identifying a subject with liver disease (e.g., acute liver failure), and treating the subject with the compositions described herein using the methods described herein.

In some embodiments, the methods of treatment described herein include a step of selecting a subject on the basis that they have a liver disease, e.g., FHF or liver fibrosis. In some embodiments, a test of liver function, e.g., as known in the art or described herein, is administered, and the subject is selected for treatment using a method described herein on the basis of the result of that test, e.g., a test result indicating that the subject has a liver disease (e.g., a liver disease associated with the loss of liver function and/or the loss or damage of hepatocytes, e.g., of parenchymal liver cells).

Thus, in some embodiments, a subject in need of treatment with the compositions and methods described herein can be selected based on, for example, serum markers of liver function. A subject in need of treatment with the methods described herein can also be selected based on diagnosis by clinician of liver disease (e.g., acute liver disease) in a subject.

Liver Disease

The term "liver disease" applies to many diseases and disorders that cause the liver to function improperly or to cease functioning, and this loss of liver function is indicative of liver disease. Thus, liver function tests are frequently used to diagnose liver disease. Examples of such tests include, but are not limited to, the following;

(1) Assays to determine the levels of serum enzymes such as lactate dehydrogenase (LDH), alkaline phosphatase (ALP), aspartate aminotransferase (AST), and alanine aminotransferase (ALT), where an increase in enzyme levels indicates liver disease. One of skill in the art will reasonably understand that these enzyme assays indicate only that the liver has been damaged. They do not assess the liver's ability to function. Other tests can be used to assay a liver's ability to function.

(2) Assays to determine serum bilirubin levels. Serum bilirubin levels are reported as total bilirubin and direct bilirubin. Normal values of total serum bilirubin are 0.1-1.0 mg·dl (e.g., about 2-18 mmol/L). Normal values of direct bilirubin are 0.0-0.2 mg/dl (0-4 mmol/L). Increases in serum bilirubin are indicative of liver disease.

(3) Assays to determine serum protein levels, for example, albumin and the globulins (e.g., alpha, beta, gamma). Normal values for total serum proteins are 6.0-8.0 g/dl (60-80 g/L). A decrease in serum albumin is indicative of liver disease. An increase in globulin is indicative of liver disease.

Other tests include prothrombin time, international normalized ratio, activated clotting time (ACT), partial thromboplastin time (PTT), prothrombin consumption time (PCT), fibrinogen, coagulation factors; alpha-fetoprotein, and alpha-fetoprotein-L3 (percent).

A clinically important type of liver disease is hepatitis. Hepatitis is an inflammation of the liver that can be caused by viruses (e.g., hepatitis virus A, B and C (HAV, HBV, and HCV, respectively), chemicals, drugs, alcohol, inherited diseases, or the patient's own immune system (autoimmune hepatitis). This inflammation can be acute and resolve within a few weeks to months, or chronic, and persist over many years. Chronic hepatitis can persist for decades before causing significant symptoms, such as cirrhosis (scarring and loss of function), liver cancer, or death.

Other important examples of the different diseases and disorders encompassed by the term "liver disease" include, but are not limited to amebic liver abscess, biliary atresia, fibrosis, cirrhosis, coccidioidomycosis, delta agent, hepatocellular carcinoma (HCC), alcoholic liver disease, primary biliary cirrhosis, pyogenic liver abscess, Reye's syndrome, sclerosing cholangitis, and Wilson's disease. In some embodiments, the compositions and methods described herein are suitable for the treatment of liver disease characterized by the loss or damage of parenchymal liver cells. In some aspects, the etiology of this can be a local or systemic inflammatory response.

Liver Failure

Liver failure occurs when large parts of the liver become damaged and the liver is no longer able to perform its normal physiological function. In some aspects, liver failure can be diagnosed using the above described assays of liver function. In some embodiments, liver failure can be diagnosed (e.g., initially diagnosed) based on a subject's symptoms. Symptoms that are associated with liver failure include, for example, one or more of the following, nausea, loss of appetite, fatigue, diarrhea, jaundice, abnormal/excessive bleeding (e.g., coagulopathy), swollen abdomen, mental disorientation or confusion (e.g., hepatic encephalopathy), sleepiness, and coma.

Chronic liver failure occurs over months to years and is most commonly caused by viruses (e.g., HBV and HCV), long-term/excessive alcohol consumption, cirrhosis, hemochromatosis, and malnutrition.

Acute liver failure is the appearance of severe complications after the first signs of liver disease (e.g., jaundice). Acute liver failure includes a number of conditions, all of which involve severe hepatocyte injury or necrosis. In most cases of acute liver failure, massive necrosis of hepatocytes occurs; however, hepatocellular failure without necrosis is characteristic of fatty liver of pregnancy and Reye's syndrome. Altered mental status (hepatic encephalopathy) and coagulopathy in the setting of a hepatic disease generally define acute liver failure. Consequently, acute liver failure is generally clinically defined as the development of coagulopathy, usually an international normalized ratio (a measure of the time it takes blood to clot compared to an average value-INR) of greater than 1.5, and any degree of mental alteration (encephalopathy) in a patient without preexisting cirrhosis and with an illness of less than 26 weeks' duration. Acute liver failure indicates that the liver has sustained severe damage resulting in the dysfunction of 80-90% of liver cells.

Acute liver failure occurs when the liver fails rapidly. Hyperacute liver failure is characterized as failure of the liver within one week. Acute liver failure is characterized as the failure of the liver within 8-28 days. Subacute liver failure is characterized as the failure of the liver within 4-12 weeks.

In some embodiments, the compositions and methods described herein are particularly suitable for the treatment of hyperacute, acute, and subacute liver failure, all of which are referred to herein as "acute liver failure." Common causes for acute liver failure include, for example, viral hepatitis, exposure to certain drugs and toxins (e.g., fluorinated hydrocarbons (e.g., trichloroethylene and tetrachloroethane), amanita phalloides (e.g., commonly found in the "death-cap mushroom"), acetaminophen (paracetamol), halothanes, sulfonamides, henytoins), cardiac-related hepatic ischemia (e.g., myocardial infarction, cardiac arrest, cardiomyopathy, and pulmonary embolism), renal failure, occlusion of hepatic venous outflow (e.g., Budd-Chiari syndrome), Wilson's disease, acute fatty liver of pregnancy, amebic abscesses, and disseminated tuberculosis.

Acute liver failure encompasses both fulminant hepatic failure (FHF) and subfulminant hepatic failure (or late-onset hepatic failure). FHF is generally used to describe the development of encephalopathy within 8 weeks of the onset of symptoms in a patient with a previously healthy liver. Subfulminant hepatic failure is reserved for patients with liver disease for up to 26 weeks prior to the development of hepatic encephalopathy.

FHF is usually defined as the severe impairment of hepatic functions in the absence of pre-existing liver disease. FHF may result from exposure of a susceptible individual to an agent capable of producing serious hepatic injury. Examples of such agents include infectious agents, excessive alcohol, hepatotoxic metabolites, and hepatotoxic compounds (e.g., drugs). Other causes include congenital abnormalities, autoimmune disease, and metabolic disease. In many cases the precise etiology of the condition is unknown (e.g., idiopathic). FHF may be diagnosed, for example, using the liver function assays described above.

Liver Fibrosis

Liver fibrosis is the excessive accumulation of extracellular matrix proteins including collagen that occurs in most types of chronic liver diseases. Advanced liver fibrosis results in cirrhosis, liver failure, and portal hypertension, and often requires liver transplantation. A key event in the etiology of liver fibrosis is inappropriate or excessive hepatic stellate cell activation (Abdel-Aziz et al., Am. J. Pathol., 137:1333-1342, 1990; Iredale et al., J. Clin. Invest., 102:538-549, 1998).

Multiple Organ Failure

Organ failure is generally defined as parenchymal cell loss associated with a local and systemic inflammatory response. More specifically, organ failure is the failure of an essential system in the body requiring medical intervention. Multiple organ dysfunction syndrome (MODS) is altered organ function in an acutely ill patient requiring medical intervention to perform homeostasis. MODS usually involves two or more organs.

MODS typically results from infection, injury (accident, surgery), hypoperfusion and hypermetabolism. Following an initiating event, an uncontrolled inflammatory response ensues, which causes tissue injury and triggers local and systemic responses. Respiratory failure is common in the first 72 hours after the original insult, hepatic failure is common in the first 5-7 days, gastrointestinal bleeding may occur at 10-15 days, and renal failure is common at 11-17 days. Mortality rates for MODS vary from 30% to 100%. There is currently no effective therapeutic regimen available to reverse established MODS.

In some embodiment, the compositions and methods described herein can be used for the treatment of organ failure, e.g., multiple organ failure.

Pharmaceutical Formulations

The compositions described herein, e.g., an MSC-CM composition and active agents isolated therefrom, can be incorporated into pharmaceutical compositions suitable for administration to a subject, e.g., a mammal, e.g., a human. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances are known. Except insofar as any conventional media or agent is incompatible with the active compound, such media can be used in the compositions of the invention. Supplementary active compounds can also be incorporated into the compositions.

A pharmaceutical composition will generally be formulated to be compatible with its intended route of administration. Solutions or suspensions used for parenteral, application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., an agent described herein) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

In one embodiment, the MSC-CM compositions are prepared with carriers that will protect the compositions against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration. In one aspect, the pharmaceutical compositions can be included as a part of a kit. Such kits are also within the scope of the present invention.

Methods of Screening

The invention provides methods for identifying the active compounds contained in an MSC-CM composition, e.g., in the heparin binding fraction of an MSC-CM composition.

In some embodiments, the active compounds contained in an MSC-CM composition, e.g., in the heparin binding fraction of an MSC-CM composition, can be obtained by systematically analyzing each of the components contained in an MSC-CM composition. Alternatively, an MSC-CM composition can be fractionated, e.g., by size and/or charge, and the active fractions can be identified. Then, each of the active fractions can be further fractionated, and the active fractions thereof identified. This can be repeated a desired number of times, and then the components of the action fraction can be identified, e.g., using methods known in the art (e.g., HPLC, mass spectrometry), and some or all of the components can then be tested for activity in the assay system. If two or more active compounds are identified, they can be combined to form a combined composition to achieve some or all of the efficacy of the complete MSC-CM, e.g., a combined composition with at least 40%, e.g., 50%, 60%, 70%, 80%, 90%, or more of the efficacy of the MSC-CM. In some embodiments, the therapeutic activity of individual components of an MSC-CM composition, or different sized fractions of an MSC-CM composition are tested using in vitro and/or in vivo assays, e.g., of hepatocyte growth, proliferation, survival, morphology, and function; a number of such assays are known in the art. For example, suitable in vitro assays can include assays to analyze hepatocyte proliferation, e.g., via BrdU incorporation; hepatocyte apoptosis, for example, by analyzing morphological changes associated with apoptosis/necrosis, or by using, e.g., TUNEL assay; RT-PCR to detect alterations in the mRNA expression levels of IL-10, IL-6, HGF, EGF, and TNF-$\alpha$; stellate cell proliferation; stellate cell apoptosis; ELISA to detect altered IL-10, TNF-$\alpha$, IL-1$\beta$, IL-6, IL-2, IL-1ra expression, and immune cell chemotaxis. Such in vivo assays include, analysis of liver histologies, e.g., following liver biopsy or following sacrifice of an animal model and animal model survival studies. The aim of such screening experimentation is to identify the biologically active component of an MSC-CM composition. The term "biologically active component of an MSC-CM composition," as used herein, refers to a component of an MSC-CM composition that produces one or more of the beneficial effects described herein, for example, modulates stellate cell signaling, promotes hepatocyte proliferation, inhibits hepatocyte cell death, or induces any change in hepatocyte mRNA or protein levels as described herein. In vitro and in vivo assays to detect such effects are known in the art and described herein.

Kits

The present invention also includes kits. In some embodiments, the kits comprise one or more doses of an MSC-CM composition. The composition, shape, and type of dosage form for the induction regimen and maintenance regimen can vary depending on a subjects requirements. For example, dosage form can be a parenteral dosage form (e.g., intravenous bolus administration), an oral dosage form, a delayed or controlled release dosage form, a topical, and a mucosal dosage form, including any combination thereof.

In a particular embodiment, a kit can contain one or more of the following in a package or container: (1) one or more doses of an MSC-CM composition, e.g., in liquid or frozen solution form or lyophilized; (2) one or more pharmaceutically acceptable buffers (3) one or more vehicles for administration of the dose, such as one or more syringes, a catheter, a pump, a hydrogel, and a depot formulation form of administration; (4) one or more additional bioactive agents for concurrent or sequential administration with an MSC-CM composition, such as supplemental active ingredients (SAI); and (5) instructions for administration. Kits in which two or more, including all, of the components (1)-(5), are found in the same container can also be used.

When a kit is supplied, the different components of the compositions included can be packaged in separate containers and admixed immediately before use. Such packaging of the components separately can permit long term storage without losing the active components' functions. When more than one bioactive agent is included in a particular kit, the bioactive agents can be (1) packaged separately and admixed separately with appropriate (similar of different, but compatible) adjuvants or excipients immediately before use, (2) packaged together and admixed together immediately before use, or (3) packaged separately and admixed together immediately before use. If the chosen compounds will remain stable after admixing, the compounds can be admixed at a time before use other than immediately before use, including, for example, minutes, hours, days, months, years, and at the time of manufacture.

The compositions included in particular kits of the present invention can be supplied in containers of any sort such that the life of the different components are optimally preserved and are not adsorbed or altered by the materials of the container. Suitable materials for these containers can include, for example, glass, organic polymers (e.g., polycarbonate and polystyrene), ceramic, metal (e.g., aluminum), an alloy, or any other material typically employed to hold similar reagents. Exemplary containers can include, without limitation, test tubes, vials, flasks, bottles, syringes, and the like.

As stated above, the kits can also be supplied with instructional materials. These instructions can be printed and/or can be supplied, without limitation, as an electronic-readable medium, such as a floppy disc, a CD-ROM, a DVD, a Zip disc, a video cassette, an audiotape, and a flash memory device. Alternatively, instructions can be published on a internet web site or can be distributed to the user as an electronic mail.

MSC Extracorporeal Bioreactor Cartridges

Also included within the present invention are EBs, and cartridges for use therein including MSCs (MSC-EB cartridges). Each cartridge can be supplied as a single cartridge for use in a extracorporeal liver support device, described above. MSC-EB cartridges can be supplied for single use with a patient for a time frame of up to 24 hours. Multiple cartridges can be supplied for use in a single subject, as dictated by a subject's treatment regimen. A number of suitable configurations of cartridges are known in the art, see, e.g., U.S. Pat. Nos. 5,270,192; 7,160,719; 6,858,146; 6,582,955; 6,759,245; Dixit and Gitnick, Eur. J. Surg. Suppl. (582):71-6 (1998); and Legallais et al., J. Memb. Sci. 181:81-95 (2001). Such cartridges can include, e.g., hollow fibers or flat plates. Generally, a semi-permeable membrane will separate the biological fluid to be treated from the cells, and such a membrane can form part of the cartridges, e.g., an exterior wall of the cartridge. The cartridges are configured to be inserted into a BAL device, e.g., as part of a bioreactor or as an entire bioreactor.

Figure 27:
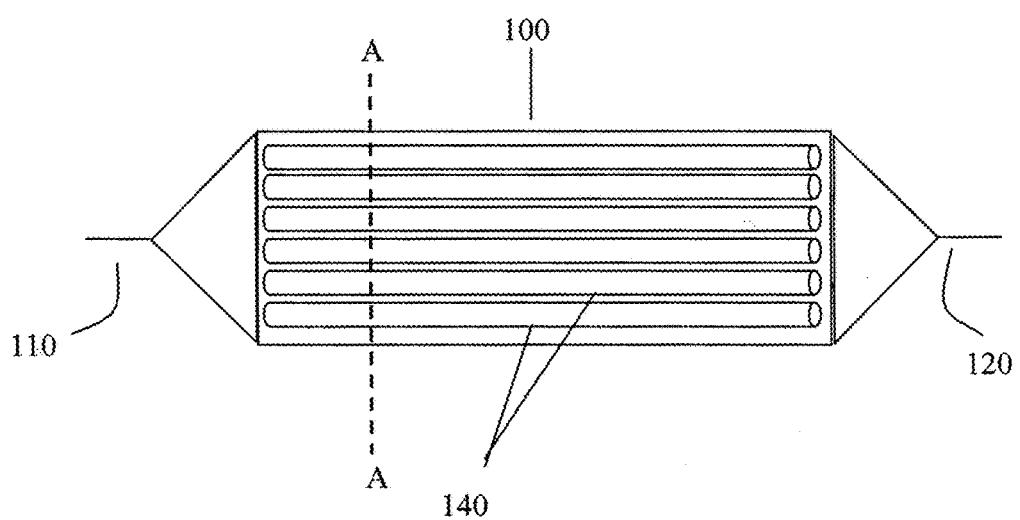
FIG. 27 is a schematic illustration of a hollow fiber bioreactor.
Figure 28:
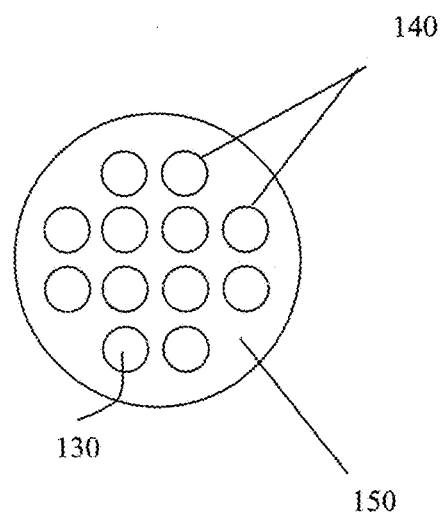
FIG. 28 is a schematic illustration of a cross section at line A-A through the hollow fiber bioreactor shown in FIG. 27.

FIG. 27 is a schematic illustration of a hollow core bioreactor cartridge 100, containing a number of hollow fibers 140, and an inlet 110 and outlet 120. The hollow fibers will be semi-permeable, allowing passage of the active factors secreted by the MSCs into the blood or plasma. FIG. 28 is a cross-sectional view of bioreactor 100 at line A-A, illustrating the hollow fibers 140, which have an interior capillary lumen 130 and are surrounded by extracapillary space 150. In hollow fiber bioreactors, the MSCs can be either in the lumen 130, while the blood or plasma flows through the extracapillary space 150, or vice-versa. In this case, the compartment including the MSCs is considered the cell compartment, while the compartment through with the blood or plasma flows is the fluid treatment compartment.

Figure 29:
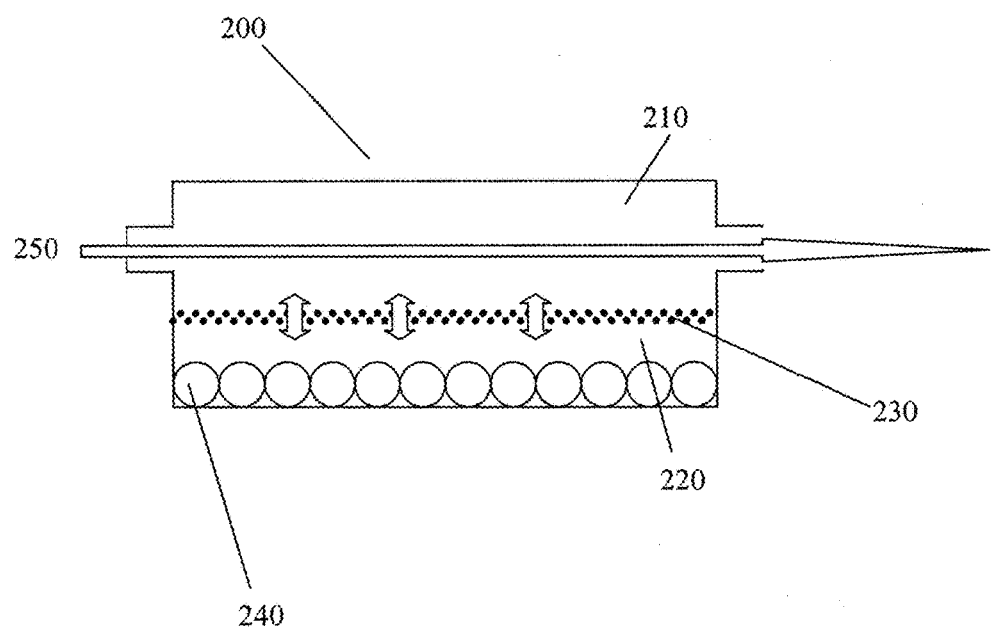
FIG. 29 is a schematic illustration of a flat-plate or two-compartment bioreactor

FIG. 29 is a schematic illustration of a flat-plate or two-compartment bioreactor 200, including a fluid treatment compartment 210 and a cell compartment 220, separated by a semi-permeable membrane 230. Blood or plasma flows through fluid treatment compartment 210 along path 250. Cell compartment 220 includes MSCs 240 (and, optionally, hepatocytes). This type of bioreactor is described in further detail in U.S. Pat. No. 6,759,254.

Also provided are kits that can contain one or more of the following in a package or container: (1) an MSC-EB cartridge; (2) one or more pharmaceutically acceptable buffers (3) instructions for installing the MSC-EB into a specific BAL. Embodiments in which two or more, including all, of the components (1)-(3), are found in the same container can also be used.

EXAMPLES

The invention is further described in the following examples, which do not limit the scope of the invention described in the claims.

Example 1—MSC Isolation, Culture and Ex Vivo Expansion

Human MSCs were isolated from commercially available bone marrow aspirates (bone marrow-derived MSCs) obtained from a single, male donor of 25 years of age (Clonetics-Poietics, Walkersville, Md.), as previously described (Mauney et al., Biomaterials, 26:6167-6175, 2005). Briefly, whole bone marrow aspirates were plated at a density of 8-10 µl aspirate/cm$^2$ on 175 cm$^2$ tissue culture flasks and grown to confluence in expansion medium at 37° C. and 5% carbon dioxide. Expansion medium consisted of Dulbecco's modified Eagle's medium supplemented with 10% fetal calf serum, 100 U/ml penicillin, 100 µg/ml streptomycin, 0.1 mM non-essential amino acids and 1 ng/ml of basic fibroblast growth factor (Life Technologies, Rockville, Md.). After 4 days of culture, non-adherent hematopoietic cells were removed by washing with PBS, and monolayers of adherent cells were cultured with medium changes 2-3 times per week. Cells were passaged using 0.25% trypsin/0.1% EDTA, subcultured at a density of 5×10$^3$ cells/cm$^2$ and used for experiments during passages 4-7. Isolated MSCs were maintained as previously described (Pittenger et al., Science, 284:143-147, 1999).

Example 2—Bone Marrow-Derived MSC Characterization

Mesenchymal stem cells (MSCs) posses several unique and well established characteristics that allow these cells to be distinguished from other cells. Such characteristics include the ability of the cells to reproducibly give rise (i.e., differentiate) to adipocytes, osteoblasts, and chondrocytes in vitro (Pittenger et al., Science, 284:143-147, 1999); and the ability of the cells to rescue mesenchymal tissue disorders in humans (Horwitz et al., Proc. Natl. Acad. Sci. USA, 99:8932-8937, 2002). In addition, human MSCs can be further identified by evaluating the cell surface expression of CD29, CD44, CD73, CD90, CD105, CD106, CD11b, CD14, CD18, CD34, CD36, and CD45 (Pittenger et al., Circ. Res., 95:9-20, 2004).

MSCs isolated using the methods described above were characterized using two distinct techniques.

First, the multipotency of bone marrow-derived MSCs was assessed in vitro by culturing the cells in (1) osteogenesis, (2) adipogenesis or (3) chondrogenesis induction medium for 2-3 weeks, with medium changes every 3 days, as follows.

(1). Osteogenic medium consisted of Iscove's modified Dulbecco's medium (IMDM) supplemented with 0.1 µM dexamethasone, 10 mM β-glycerol phosphate, 0.2 mM ascorbic acid (AsA), 100 U/ml penicillin and 100 µg/ml streptomycin.

(2). Adipogenesis medium consisted of IMDM supplemented with 0.5 mM 3-isobutyl-1-methylxanthine, 1 µM hydrocortisone, 0.1 mM indomethacin, 10% rabbit serum, 100 U/ml penicillin and 100 µg/ml streptomycin.

(3). For chondrogenesis studies, cells were transferred into a 15-mL polypropylene tube and centrifuged at 1000 rpm for 5 minutes to form a pelleted micromass that was then treated with chondrogenic medium. Chondrogenesis medium consisted of high-glucose DMEM (Chemicon International, Temecula, Calif.) supplemented with 0.1 µM dexamethasone, 50 µg/mL AsA, 100 µg/mL sodium pyruvate, 40 µg/mL praline, 10 ng/mL TGF-$β_1$, 50 mg/mL ITS+ premix (Becton Dickinson; 6.25 µg/mL insulin, 6.25 µg/mL transferring, 6.25 ng/mL selenious acid, 1.25 mg/mL bovine serum albumin, and 5.35 mg/mL linoleic acid), 100 U/ml penicillin and 100 µg/ml streptomycin.

The phenotype of differentiated cells was evaluated after 2-3 weeks of induction, as follows.

(1). Mineral content under osteogenic conditions was determined using the Von Kossa stain, as follows. Briefly, cells were fixed with 4% paraformaldehyde for 15 minutes, washed twice with PBS, stained with 1% silver nitrate under a 100 W light for 60 minutes and washed with deionized (DI) water.

(2). Lipid accumulation after adipogenic conditions was determined by oil Red 0 staining, as follows. Briefly, cells were fixed with 4% paraformaldehyde, washed twice with PBS, stained with oil-Red 0 for 15 minutes and washed with DI water.

(3). Proteoglycan content after chondrogenic conditions was assessed by safranin-O staining, as follows. Briefly, the micropellet was fixed in 4% paraformaldehyde, serially diluted in ethanol and embedded in paraffin blocks. Blocks were sectioned and stained with safranin-O.

All images were captured on an Nikon Eclipse E800 Upright Microscope.

The results showed that osteogenesis, adipogenesis, and chondrogenesis were induced in their respective induction mediums. The staining for osteogenesis, adipogenesis, and chondrogenesis is visualized by mineral deposition, lipid droplets, and chondroitin sulfate, respectively.

Second, MSCs were immunophenotyped by flow cytometry (FACS Calibur, Becton Dickinson, Franklin Lakes, N.J.). The surface antigen panel included CD14, CD34, CD44, CD45, and CD106 (BD Pharmingen, Franklin Lakes, N.J.).

As expected, the surface antigen profile of the isolated MSCs was CD14−, CD105+, CD34−, CD45−, CD106+ and CD44+. These observations are consistent with previous reports of undifferentiated MSC surface marker expression (Pittenger et al., Circ. Res., 95:9-20, 2004).

Thus, the methods used were suitable for isolation of MSCs.

Example 3—Immunomodulation of Stellate Cells by MSCs

This example demonstrates that MSCs are capable of modulating activated hepatic stellate cells (SCs), likely via paracrine mechanisms.

Liver fibrosis, the precursor to cirrhosis, is generally thought to be the result of an imbalance in extracellular matrix (ECM) synthesis and degradation mediated primarily by SCs.

SCs are pericytes frequently found in the perisinusoidal space located between the sinusoids and hepatocytes in the liver. In a normal and healthy liver, SCs are quiescent and primarily involved vitamin A storage. Following liver injury, SCs undergo a phenotypic switch into proliferative, α-smooth muscle actin positive, myofibroblast-like cells capable of increased collagen synthesis. SCs can be easily distinguished by the large lipid droplets observed in the cytoplasm of these cells.

In vivo activation of SCs is divided into a fibrogenic and hyperplastic response that is mediated by many autocrine and paracrine signals. Spontaneous resolution of liver fibrosis has been reported in different rat models of chronic liver injury (Abdel-Aziz, et al., Am. J. Pathol., 137:1333-1342, 1990; Iredale et al., J. Clin. Invest. 102:538-549, 1998). This resolution has been correlated with decreased synthesis of type I collagen and tissue inhibitor of matrix metalloproteinases (TIMP) 1 and 2 transcripts, with a concomitant decrease in the number of α-SMA positive SCs (Iredale et al., J. Clin. Invest. 102:538-549, 1998). It is unclear whether the decrease in the number of activated SCs is due to selective apoptosis or reversion to a quiescent state by microenvironmental cues.

These data demonstrate that MSC therapy is useful in the treatment of disorders caused by activated SCs in a subject, for example, liver fibrosis.

3A—SC Isolation

Primary rat SCs were isolated from 2-3 month-old adult female Lewis rats (Charles River Laboratories, Wilmington, Mass.) weighing 180-200 g, as previously reported in detail for hepatocyte isolation (Dunn et al., FASEB J., 3:174-177, 1989). Briefly, the supernatant from the hepatocyte purification steps, containing the non-parenchymal liver cells were obtained and treated with DNAse I for 15 minutes at 37° C., centrifuged at 300 g for 20 minutes, and then resuspended in PBS. This cell suspension was subjected to a density gradient separation by gently layering the suspension on top of a discontinuous 40%-60% isotonic Percoll gradient. The layers were then centrifuged at 900 g for 25 minutes. The lowest density layer, enriched in SCs, was then removed, diluted with PBS and centrifuged at 900 g for 25 minutes. The cells were resuspended in SC medium (Dulbecco's modified Eagle's medium supplemented with 10% FBS, 100 U/ml penicillin and 100 µg/ml streptomycin) and cultured on 175 cm² tissue culture flasks. SCs were cultured for 10-14 days on tissue culture plastic, which led to their activation, before use in experiments. The purity and differentiation of SC cultures were assessed by performing immunofluorescence for desmin, a myofibroblast marker, and α-SMA, a marker for myofibroblasts in a more advanced state of differentiation.

Immunofluorescent detection was performed after a 15 minute fixation in 4% paraformaldehyde solution prepared in phosphate buffered saline (PBS), followed by a single wash with PBS. All steps were performed at room temperature. Cells were permeabilized by incubating with blocking buffer (10% normal horse serum, 0.025% Triton X-100 and 0.5% dimethylsulfoxide in PBS) for 45 minutes. Subsequently, the cells were incubated with mouse monoclonal anti-α-SMA antibody (GeneTex Inc, San Antonio, Tex.; 1:100 dilution) or goat polyclonal anti-desmin antibody (Santa Cruz Biotechnology-clone C18; 1:100 dilution) in blocking buffer for 60 minutes. After washing three times with blocking buffer, incubation with rhodamine red-X conjugated goat anti-mouse secondary antibody (1:250 dilution) or FITC-conjugated donkey anti-goat secondary antibody (1:500 dilution; Jackson ImmunoResearch Laboratories, West Grove, Pa.) was performed for 60 minutes, respectively. Three washes were performed with blocking buffer, incubating with 5 μg/mL of 4',6-diamidino-2-phenylindole (DAPI; Molecular Probes, Leiden, Netherlands) for 5 minutes during the first wash. Samples without primary antibody were used as negative controls. Fluorescent and phase-contrast microscopy were performed on a Zeiss AXIOVERT 200 M Inverted Microscope.

All cells stained positively for both desmin and α-SMA following 10 days of culture, demonstrating successful isolation and purification of SC cells.

3B—MSC and SC Culture Systems

Isolated SCs were co-cultured with MSCs, isolated and characterized as described in Example 1 and Example 2, using direct or indirect systems, as follows.

Direct Co-culture System: SCs and MSCs were seeded together at a ratio of 1:1 in each well of a six-well plate (Corning Costar, Acton, Mass.)

Indirect co-culture System: SCs and MSCs were co-cultured using a Transwell configuration. Approximately $1.0 \times 10^5$ SCs were seeded in the lower chamber with $0\text{-}1.0 \times 10^5$ MSCs seeded on the membrane inserts. MSCs were replaced with human umbilical vein endothelial cells for controls. Co-cultures were maintained in SC medium for 4 days.

3C—MSCs Inhibit Collagen Synthesis in Activated Stellate Cells

SC secretion of procollagen type-I C-peptide (PIP), a peptide fragment cleaved from precursor collagen upon extracellular secretion, was measured after four days of indirect co-culture as a function of MSC to SC ratio, with the number of SCs remaining constant Collagen synthesis was quantified using an ELISA for procollagen type-I C-peptide (Takara-Bio Inc., Shiga, Japan). After the co-culture period, the Transwell insert containing MSCs was removed and the medium on the SCs was replaced with fresh medium. Twenty-four hours later, medium was collected and procollagen type-I C-peptide concentration was measured by ELISA.

PIP levels secreted by activated SCs (101±11 pg/106 cells/day) were significantly reduced at a MSC:SC co-culture ratio of 1:10 (41±18 pg/106 cells/day; p=0.0491), with a 66% reduction at a 1:1 co-culture ratio (34±5 pg/106 cells/day; p=0.004).

Reduced PIP secretion was not observed in co-cultures of SCs with human umbilical vein endothelial cells (MVEC), suggesting a MSC-specific effect. These results suggest that soluble factors released by MSCs inhibit the synthesis of procollagen in activated SCs.

3D—MSCs Induce Apoptosis in Activated SCs

The decrease in hepatic fibrosis observed after transplantation of MSCs is accompanied by a reduction in the number α-SMA+(activated stellate) cells observed by immunohistological staining (Sakaida et al., Hepatology, 40:1304-1311, 2004; Fang et al., Transplantation, 78:83-88, 2004; Zhao et al., World J. Gastroenterol., 26:6167-6175, 2005). The mechanism by which the reduction in the number of activated stellate cells occurs is unclear; there is evidence for decreased proliferative capacity, a reversion to a quiescent phenotype and for apoptotic cell death. Therefore, we examined the fate of activated SCs indirectly co-cultured with MSCs by measuring the extent of SC dedifferentiation, proliferation and death.

SC dedifferentiation or reversion back to a quiescent state was determined by analysis α-SMA expression, as described above. The expression of α-SMA was not decreased after co-culture. This observation suggests that SCs do not revert to a quiescent phenotype in the presence of MSCs.

SC proliferation was assessed using flow cytometry to quantify the population of SCs entering the S-phase of the cell cycle, as measured by BrdU incorporation, after co-culture with MSCs.

Briefly, twenty-four hours prior to analysis, the Transwell insert containing MSCs was removed and SC cultures were treated with 10 μM BrdU. Cells were then washed with PBS three times, trypsinized and centrifuged at 1200 rpm for 5 minutes. For fixation, the pellet was resuspended in 70% ethanol for 45 minutes at room temperature, centrifuged and washed twice with PBS. Cells were incubated with 4 M HCl for 15 minutes at room temperature, centrifuged, washed twice with PBS and incubated with a blocking buffer composed of PBS and 10% FBS for 10 minutes. Cells were then incubated with anti-BrdU antibody conjugated to Alexa-Fluor 488 dye for 60 minutes at 37° C., centrifuged and washed with PBS. Negative controls consisted of cells incubated without the antibody. Fluorescently labeled cells were analyzed by flow cytometry.

As shown in FIG. 1, a decline, from 30±9% to 15±4%, in BrdU+ SCs was observed at a 1:1 co-culture ratio (p=0.043).

Microscopic observation of indirect co-cultures indicated a decrease in the number of SCs adhering to the polystyrene plate. To determine if apoptosis accounted for the observed changes in SC number after co-culture, Annexin-V-FITC staining and flow cytometry were used.

Briefly, quantification of cell apoptosis/necrosis was determined using the Annexin-V FLUOS kit (Roche, Indianapolis, Ind.) as per vendor instructions. After co-culture, SCs were recovered and stained with Annexin V for 20 minutes and analyzed using flow cytometry. Serum deprived SCs served as a positive control for apoptosis. Results were gated based on fluorescent signals greater than SC autofluorescence.

In SCs cultured alone, there was a basal level of apoptosis (25%). Using the indirect co-culture system with a ratio of 1:1, there was an approximate 2.5 fold increase in apoptosis (55%). Co-culture with fibroblasts resulted in a level of apoptosis that was similar to SCs alone (32%), demonstrating that the pro-apoptotic effect was MSC-specific.

TABLE 1

Apoptosis of Activated SCs as a Function of MSC Number

| MSC:SC ratio | Trial 1 | Trial 2 | Trial 3 | Trial 4 | Mean (%) | St. Dev. (%) | p-value |
|---|---|---|---|---|---|---|---|
| 0 | 12.24 | 18.47 | 16.23 | 15.87 | 15.68 | 2.54 | — |
| 1:10³ | 18.37 | 34.16 | 22.24 | 14.95 | 22.43 | 8.37 | 0.1008 |
| 1:10² | 25.54 | 26.53 | 26.00 | 25.96 | 26.01 | 0.41 | $8.63 \times 10^{-3}$ |
| 1:10 | 34.22 | 23.2 | 36.31 | 38.08 | 32.95 | 6.69 | $3.56 \times 10^{-3}$ |
| 1:1 | 53.53 | 44.71 | 45.85 | 36.92 | 42.97 | 11.64 | $6.98 \times 10^{-4}$ |

As shown in Table 1, significant SC death also occurred at MSC:SC co-culture ratios of 1:100 or greater, suggesting that small numbers of MSCs can release potent pro-apoptotic molecules that induce SC death.

Taken together, these in vitro results imply that transplantation of MSCs in vivo can ameliorate or resolve hepatic fibrosis through a mechanism involving a highly selective pro-apoptotic effect on activated SCs.

3E—MSCs Secrete IL-10 and TNF-α

MSCs were exposed to IL-1, IL-6, or tumor necrosis factor-α(TNF-α), all of which are cytokines known to be involved in liver fibrosis, for 24 hours. IL-10 protein secretion and mRNA levels were the determined by enzyme-linked-immunosorbent-assay (ELISA) and RT-PCR, respectively.

Briefly, human MSCs were treated with 2.5 ng/ml IL-6 (R&D Systems, Minneapolis, Minn.), 5 ng/ml IL-1 (R&D Systems, Minneapolis, Minn.), or 25 ng/ml TNF-α (R&D Systems, Minneapolis, Minn.) supplemented MSC expansion medium for 24 hours. MSCs cultured in expansion medium served as a negative control. After treatment, cells were harvested and analyzed for changes in gene expression.

Quantification of human IL-10 was determined using an ELISA as per vendor instructions (Endogen, Rockford, Ill.). Supernatants were sampled after 48 hours of co-culture and stored at −20° C. until analysis.

RNA was extracted from 0.1-1.0×10$^6$ MSCs using the NUCLEOSPIN RNA purification kit (BD Biosciences, Palo Alto, Calif.) per the manufacturer's instructions. Approximately 1 µg of total mRNA was reverse transcribed to cDNA using the ONESTEP RT-PCR Kit (Qiagen, Valencia, Calif.) per manufacturer's instructions and amplified in a Perkin Elmer-Cetus Thermal Cycler 480. Cycling conditions were: 1) 50° C. for 30 minutes; 2) 95° C. for 15 minutes; 3) 30 cycles at 94° C. for 30 seconds, 55° C. for 30 seconds, and 72° C. for 1 minute; and 4) a final extension step at 72° C. for 10 minutes. IL-10 was amplified using a combination of the sense and antisense oligonucleotides SEQ ID NO:1 and SEQ ID NO:2, respectively, to yield a 364 base pair (bp) PCR product. Glyceraldehyde 3-phosphate dehydrogenase (GAPDH) was amplified using a combination of the sense and antisense oligonucleotides SEQ ID NO:3 and SEQ ID NO:4, respectively, to yield a 238 bp PCR product.

```
                                        SEQ ID NO: 1
    5'-AAGCCTGACCACGCTTTCTA-3'

SEQ ID NO: 2
    5'-GTAGAGCGGGGTTTCACCA-3'

SEQ ID NO: 3
    5'-GAGTCAACGGATTTGGTCGT-3'

SEQ ID NO: 4
    5'-TTGATTTTGGAGGGATCTCG-3'
```

As shown in FIGS. 2-3, exposure to IL-6 (2.5 ng/ml) or TNF-α (25 ng/ml), cytokines which are significantly elevated in liver injury models, led to the upregulation of both IL-10 mRNA (FIG. 2) and protein secretion into the culture medium (FIG. 3).

Figure 4:
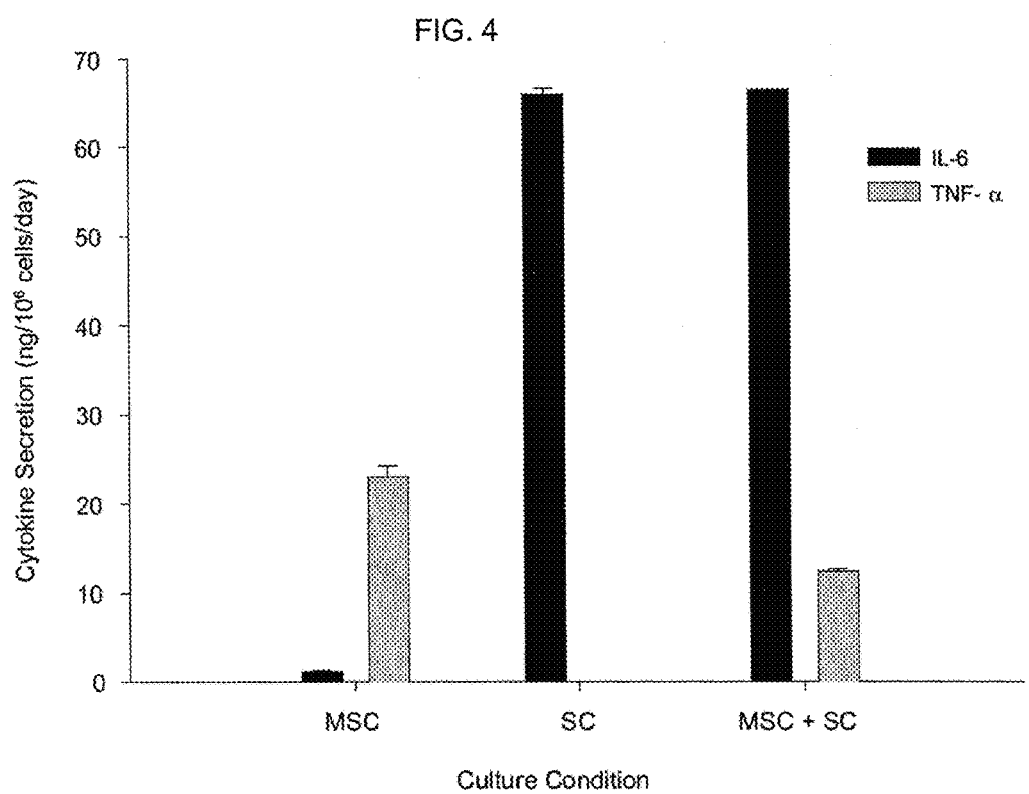
FIG. 4 is a bar graph showing cytokine secretion in monoculture and direct co-culture of SCs and MSCs (1:1 ratio). IL-6 and TNF-α concentrations were measured by ELISA with species-specific antibodies after 2 days of culture. Results are the mean of two experiments performed in triplicate. Error bars are standard deviation.

As shown in FIG. 4, IL-6 and TNF-α were both found to be present in the SC/MSC direct co-culture system, as determined by ELISA, as described above. IL-6 was secreted by activated SCs (65±1 pg/10$^6$ cells/day), while TNF-α was secreted by MSCs (23±1 pg/10$^6$ cells/day).

As shown in FIG. 5, activated SCs are capable of inducing MSCs to secrete IL-10 when the cells are directly co-cultured at a ratio of 1:1 (54 pg/10$^6$ cells/day). These levels were similar to the levels observed in FIG. 6.

As shown in FIG. 6, at a MSC:SC ratio of at least 1:10, SCs were capable of inducing elevated IL-10 mRNA expression in MSCs when cultured indirectly using the above described Transwell configuration. Using the same system, IL-10 protein secretion increased to 32±7 pg/10$^6$ cells/day (p<0.01).

Since both IL-6 and TNF-α were detected in MSC-SC co-cultures, neutralization by monoclonal antibodies was performed to determine the role of IL-6 and TNF-α on the release of IL-10 by MSCs.

Neutralization of specific cytokines was performed during indirect co-cultures. For all neutralization experiments, the ratio of MSCs to SCs was 1:1. Anti-human IL-10 (BioLegend, San Diego, Calif.), TNF-α, (BioLegend, San Diego, Calif.), or HGF and anti-rat IL-6 (Cell Sciences, Canton, Mass.) were diluted in SC medium based on the half maximal inhibition concentrations given by the manufacturer. Fresh medium with neutralizing antibodies was added after 48 hours of co-culture.

Figure 7:
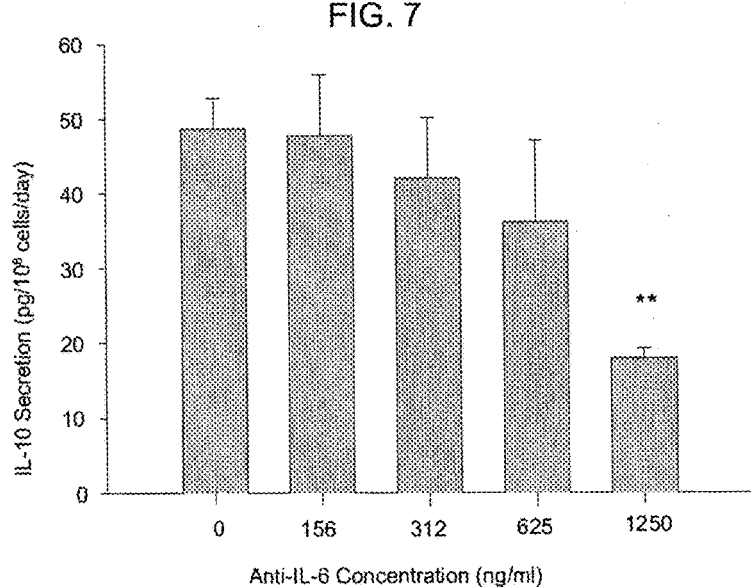
FIG. 7 is a bar graphs showing the inhibition of IL-10 secretion by MSCs in direct (1:1) co-culture with activated SCs after treatment with anti-IL-6 neutralizing antibody. Results are the mean of two experiments performed in triplicate. Error bars are standard deviation. $**p<0.01$ compared to no antibody.

As shown in FIG. 7, a significant decrease in IL-10 release (48±4 to 18±1 pg/10$^6$ cells/day; p<0.01) was observed when the indirect co-cultures were treated with 1250 ng/ml of anti-IL-6 neutralizing antibody. No significant difference was observed after treatment with anti-TNF-α neutralizing antibody. Taken together, these data imply that activated SCs secrete IL-6, which induces MSCs to secrete IL-10.

3F—MSCs Inhibit Activated SC Collagen Synthesis and Proliferation Via IL-10 and TNF-α Paracrine Signaling To determine if the previously observed suppression of collagen synthesis and proliferation in activated SCs, after indirect co-culture with MSCs, was mediated by MSC-derived IL-10 and TNF-α, levels of PIP secretion by activated SCs was measured after four days of indirect co-culture with MSCs in the presence of neutralizing antibodies to IL-10, TNF-α, or both.

Partial normalization of PIP secretion was observed after neutralization of IL-10 or TNF-α at antibody concentrations of 1000 ng/ml and 500 ug/ml or greater, respectively. Neutralization of both IL-10 and TNF-α in co-culture led to a synergistic rise in PIP levels from 79±9 pg/10$^6$ cells/day to 215±20 pg/10$^6$ cells/day (p=0.002) at maximal antibody concentrations.

The effects of MSC-derived TNF-α and IL-10 on the proliferation of activated SCs was analyzed. Neutralizing the effects of IL-10 in a 1:1 co-culture led to a marginal rise in the number of BrdU-positive cells, from 12% to 15% at the maximum antibody concentration. Neutralization of TNF-α resulted in a more significant effect on proliferation with an increase in BrdU-positive cells from 13% to 33% (p=0.0197). Neutralization of both cytokines led to the most significant increase proliferation population (13% to 44%).

These data suggest a synergy between TNF-α and IL-10 signaling pathways (p=0.009).

3G—MSC-Derived Hepatocyte Growth Factor (HGF) Induces Apoptosis in Activated SCs Given the observation that a relatively small number of MSCs could cause SC apoptosis, indirect co-culture supernatants were analyzed for potent pro-apoptotic signals.

Figure 8:
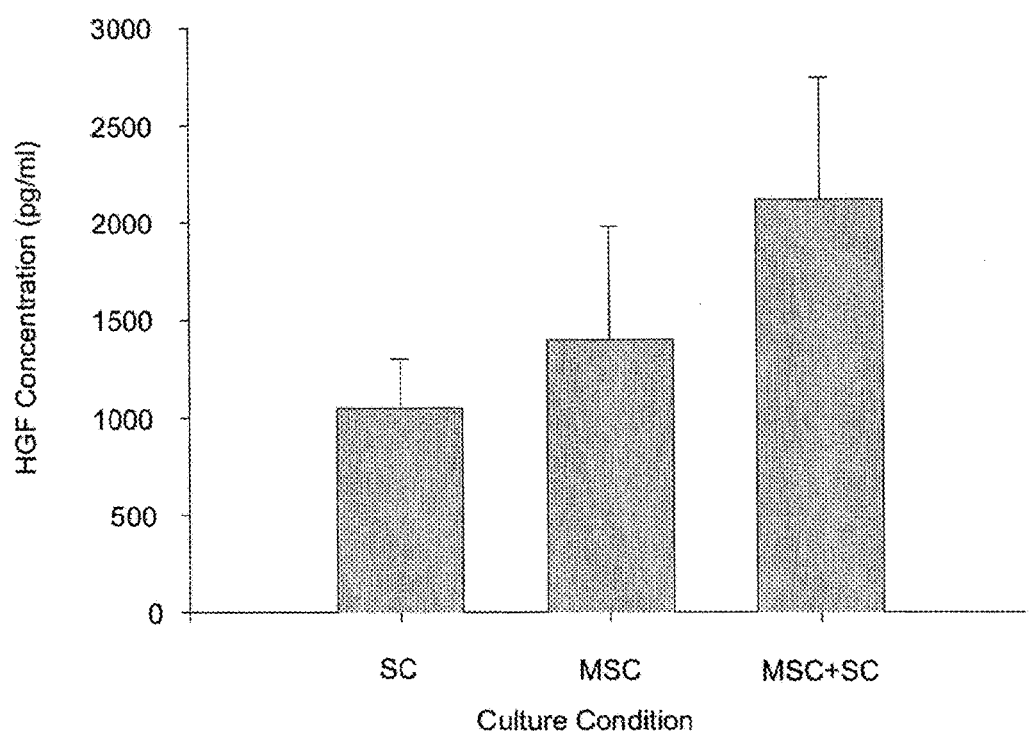
FIG. 8 is a bar graph showing Hepatocyte Growth Factor (HGF) secretion after 2 days of monoculture or 1:1 direct co-culture of SCs and MSCs. Results are the mean of two experiments performed in triplicate.

As shown in FIG. 8, a considerable amount of hepatocyte growth factor (HGF) in mono- and co-cultures was detected and was produced at approximately equivalent levels by both SCs and MSCs.

TABLE 2

Apoptosis of Activated SCs as a Function of HGF Neutralization

| Anti-HGF (µg ml$^{-1}$) | Trial 1 | Trial 2 | Trial 3 | Trial 4 | Mean (%) | St. Dev. (%) | p-value |
|---|---|---|---|---|---|---|---|
| 0    | 53.53 | 44.71 | 45.85 | 36.92 | 42.97 | 11.64 | —      |
| 0.05 | 43.66 | 22.11 | 25.67 | 21.5  | 28.24 | 10.45 | 0.2056 |
| 0.5  | 39.32 | 11.87 | 19.26 | 23.94 | 23.59 | 11.60 | 0.1136 |
| 1.5  | 18.47 | 21.17 | 15.9  | 17.25 | 18.20 | 2.24  | 0.0390 |
| 5.0  | 13.81 | 17.76 | 14.38 | —     | 15.32 | 2.14  | 0.0413 |

As shown in Table 2, a decrease in apoptosis was observed as a function of neutralizing antibody to HGF. This decrease in apoptosis did not occur when the cultures were incubated with a control antibody with no HGF specificity. These data support a role for MSC-derived HGF in accelerating the rate of SC apoptosis.

In summary, the data presented in Example 3 demonstrates that MSCs are capable of inhibiting the proliferative and fibrogenic function of activated SCs in a paracrine manner and as a function of MSC number. This inhibition is caused by MSC-derived IL-10 and TNF-α, which act synergistically. The secretion of IL-10 by MSCs is a dynamic response to IL-6 secretion by activated SCs. Secretion of IL-10 by MSCs in response to TNF-α was observed after exogenous stimulation, but not during mono- or co-culture. This result likely reflects the high levels of stimulation used in vitro (e.g., approximately 25 ng ml$^{-1}$) compared to the low levels measured in co-culture (e.g., approximately 2.5 ng ml$^{-1}$). This observation strongly implies that a threshold concentration of TNF-α is necessary to induce IL-10 expression in MSCs. IL-6 and TNF-α also increase nuclear factor (NF)-kappaB signaling in various cells types. Thus, NF-kappaB may also play a role in MSC cytokine expression during inflammation.

Figure 9:
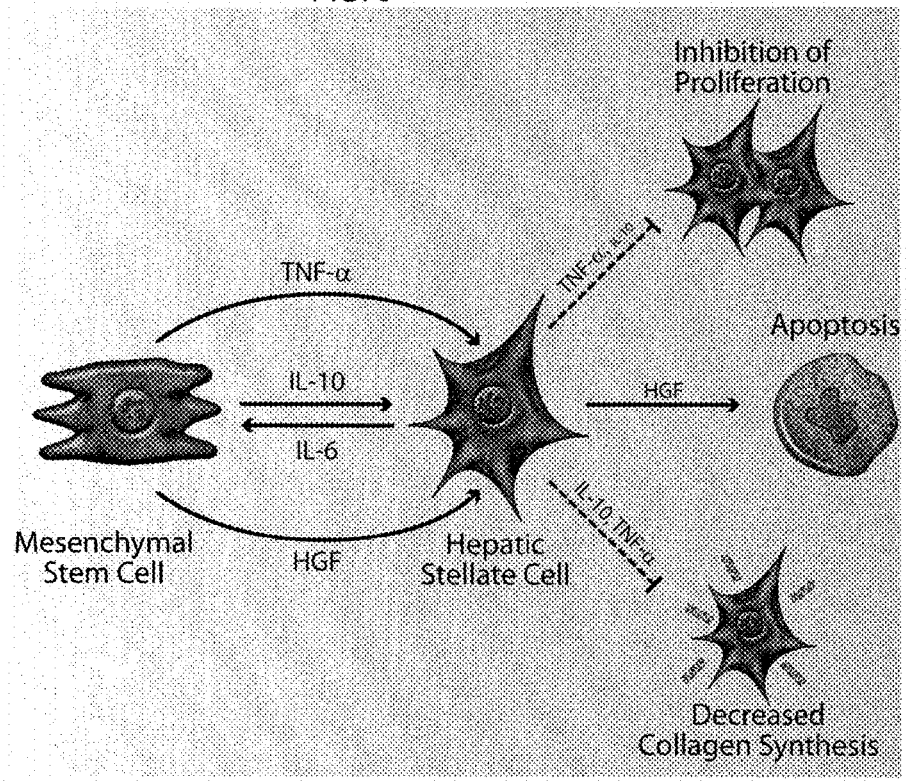
FIG. 9 is a schematic model of the paracrine effects of MSC-derived factors on activated SCs. Autocrine factors synthesized by SCs are not represented in this model. Release of IL-6 by activated SCs leads to the secretion of IL-10 by MSCs. Induced IL-10, along with constitutively secreted TNF-α, inhibit of SC proliferation and collagen synthesis. The marginal effect of IL-10 on SC proliferation is denoted by the smaller font size. SCs undergo apoptosis after co-culture with MSCs due to increased levels of HGF.

MSCs also induced apoptosis in activated SCs, which is mediated by HGF. The effect of MSC-derived HGF and IL-10 is likely supplementary to the autocrine signaling of these proteins in SCs. The above described data are summarized in FIG. 9.

These studies demonstrate for the first time that MSCs act through multiple mechanisms to coordinate a dynamic, integrated response to inflammation, particularly fibrosis. Similar immunoprotective mechanisms may also influence the phenotype of hepatocytes, kupffer cells, sinusoidal endothelial cells, and immune cells that infiltrate the liver during inflammation.

Example 4—Acellular MSC Based Therapy—Generation of Acellular MSC Conditioned Medium (MSC-CM)

This example demonstrates the production of an MSC-CM composition.

MSCs were isolated and characterized as described in Example 1 and Example 2. In some embodiments, MSCs were characterized based on the detection of cell surface expressed markers (e.g., CD14−, CD105+, CD34−, CD45−, CD106+ and CD44+). Cells that did not satisfy the characterization criterion described in Example 2 were discarded. In some embodiments, human MSCs were provided by the Tulane Center for Gene Therapy.

An MSC-CM composition was generated by culturing MSCs up to a maximum cell density of 70-80% confluency. Cells were not permitted to undergo differentiation. In other words, MSCs were maintained in an undifferentiated state. In some embodiments, MSC differentiation was monitored using the characterization criterion described in Example 2. In some embodiments, a 70-80% confluence corresponds to 1×10$^6$ MSCs per 175 cm$^2$ tissue culture grade flask. In some embodiments, an MSC-CM composition was generated using 2×10$^6$ MSCs, which were obtained using two 175 cm$^2$ tissue culture grade flasks with each flask containing 1×10$^6$ cells.

MSC-CM was prepared as follows;

(1) 70-80% confluent MSCs were washed thoroughly with phosphate buffered saline (PBS);

(2) MSCs from (1) were cultured in 15 ml serum free DMEM supplemented with 0.05% bovine serum albumin to prevent protein aggregation;

(3) MSCs were cultured for 24 hours;

(4) culture media was collected from (3); and (5) collected culture media was concentrated 25-fold (e.g., 25 times) using ultrafiltration with a 3 kD cutoff.

The MSC-CM composition was concentrated using ultrafiltration units (Amicon Ultra-PL 3, Millipore, Bedford, Mass., USA).

The MSC-CM composition was fractionated into heparin binding and non-heparin binding fractions. For fractionation experiments, concentrated an MSC-CM composition was passed over a heparin-agarose column per vendor's instructions. Briefly, columns were primed with 10 equivalents of binding buffer (10 mM sodium phosphate, pH 7.0). The sample was applied, followed by 10 equivalent volumes of binding buffer, which was considered as the heparin unbound fraction. The bound fraction was eluted with 10 volumes of binding buffer supplemented with 1 M NaCl. Flow-through and eluted fractions were collected separately. Flow-through and eluted fractions were collected and reconcentrated, as described above.

Example 5—Experimental FHF Induction and Treatment Regimens

This example demonstrates the induction of FHF in an experimental animal model.

The induction of fulminant hepatic failure (FHF) is previously reported (Shinoda et al., J. Surg. Res., 137:130-140, 2007). Briefly, male Sprague-Dawley rats weighing 250-300 g were used for FHF experiments. Hepatocytes were isolated from 150-200 g female Lewis. All animals (Charles River Laboratories, Boston, Mass.) were handled in accordance with the guidelines set forth by the Committee on Laboratory Resources, National Institutes of Health.

FHF was induced using two injections of Gal-N(Sigma Aldrich, St Louis, Mo.), freshly dissolved in 0.9% NaCl solution and administered i.p. with a 12-hour interval. Different dosages of Gal-N were chosen for tissue analysis (0.6 g/kg) and survival studies (1.2 g/kg), based on our previous studies. When appropriate, twenty-four hours after FHF induction 0.9 ml of MSC-CM or 0.9% NaCl solution (vehicle control) was injected through the penile vein under ketamine/xylazine anesthesia (110 mg/kg and 0.4 mg/kg i.p. respectively). Animals receiving 0.6 g/kg were sacrificed 36 hours later for tissue collection. Survival was monitored every 12 hours for 28 days.

Example 6—MSC-CM Therapy Inhibits Gross Liver Change

This example demonstrated an hepatoprotective effect of MSC-CM.

Gal-N induced FHF is typically accompanied by characteristic changes in gross appearance of the liver consisting of increased pallor and a soft and shrunken consistency.

FHF was induced in Sprague-Dawley rats using Gal-N, as described in Example 5. Animals were treated with systemic infusions of concentrated MSC-CM or with vehicle (control). A sublethal dose of Gal-N (0.6 g/kg) was used for tissue analysis 36 hours after treatment and 1.2 g/kg Gal-N was administered for survival studies. Liver histologies were analyzed as follows.

Formalin-fixed, paraffin-embedded liver specimens were sectioned at 4 μm and stained with hematoxylin & eosin (H&E). Histological assessment was performed by a blinded observer, who scored the liver sections using the following criteria: "0" for normal histology, "1" for minor hepatocellular death and inflammation, "2" for widely distributed patchy necrosis with inflammation, "3" for complete lobular disruption and diffuse hepatocyte necrosis with panlobular inflammation, and "4" for mortality.

In this trial, one of four control animals died before animals were sacrificed, confirming that the extent of injury in the used model can be rapidly fatal. Necropsy was not performed on this animal, but based on our prior experience with this model we expect that gross appearance was abnormal.

Two of the 3 remaining control livers, which were soft and shrunken with an abnormal pale appearance and a rough textured surface. The liver of one vehicle treated rat appeared normal. In contrast, none of the 4 MSC-CM treated livers demonstrated gross pathological changes. In contrast to the affected control livers, the livers from MSC-CM treated animals were larger with a dark coloration and a glossy surface typical of a healthy liver.

Figure 10:
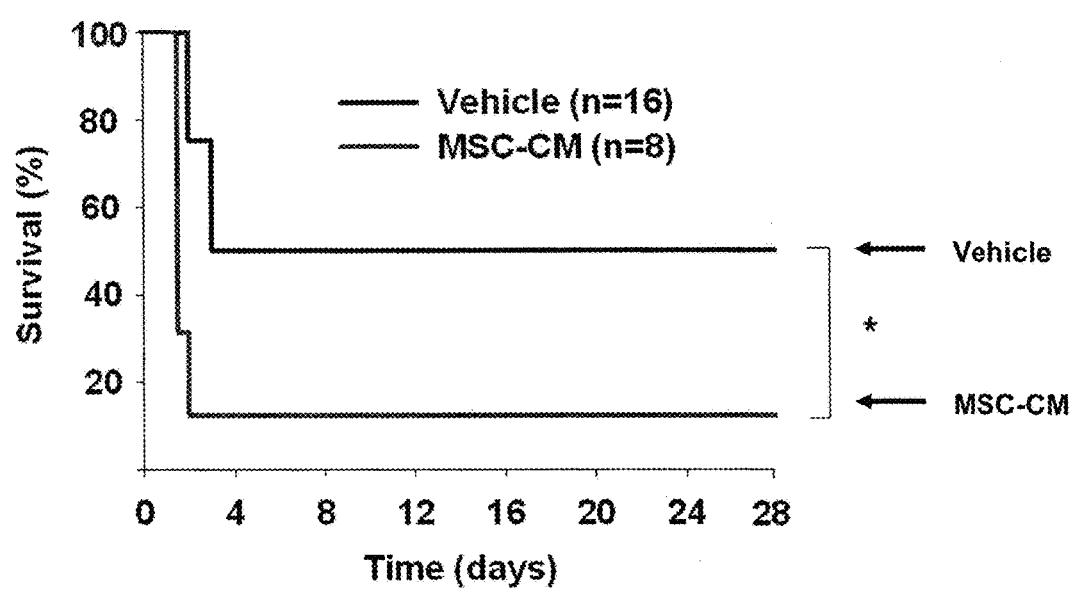
FIG. 10 is a Kaplan-Meier survival analysis of Gal-N rats after MSC-CM treatment. $*p=0.017$ (Log Rank). MSC-CM, mesenchymal stem cell-conditioned medium; FHF, fulminant hepatic failure; Gal-N, D-galactosamine.
Figures 11A, 11B, 11C, 11D, 11E, 11F:
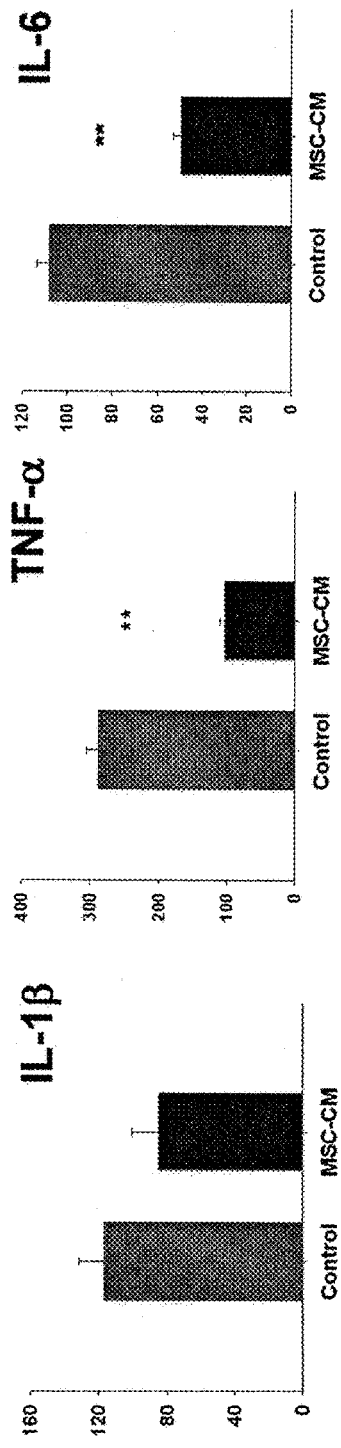
FIGS. 11A-11F are bar graphs showing systemic levels of (11A) IL-1β; (11B) TNF-α; (11C) IL-6; (11D) IL-2; (11E) IL-1ra; and (11F) IL-10 following exposure to Gal-N. Data shown are mean±standard deviation of experiments performed in triplicate. $*p<0.05$, $**p<0.001$.

As shown in FIG. 10, two of 16 control animals (12.5%) survived the entire observation period. All other vehicle treated rats (87.5%) died within 60 hours. In the MSC-CM group, 2 of 8 animals (25%) died in the first 60 hours. Four (50%) survived the 28-day study period. Overall, MSC-CM treatment significantly improved survival of Gal-N induced FHF (p=0.017).

Example 7—CM Treatment Downregulates Systemic Inflammation

Severe liver injury (e.g., following Gal-N treatment) can result in a local and systemic inflammatory response that can ultimately lead to multi-organ failure and death. To investigate the systemic inflammatory response in animals exposed to Gal-N, serum samples were collected from Gal-N animals 36 hours after treatment with a systemic injection of MSC-CM (n=4) or vehicle (n=3) and analyzed by ELISA, as follows.

Blood samples were centrifuged at 12,000 rpm for 15 min in a microcentrifuge and serum was collected for analysis. Quantification of rat IL-1β, TNF-α, IL-6, IL-2, interleukin-1 receptor antagonist (IL-1ra) and IL-10 was determined using ELISA per manufacturer's instructions (R&D Systems, Minneapolis, Minn.).

As shown in FIGS. 11A-F, analysis of systemic cytokine levels revealed a non-significant decrease for IL-1β (p=0.054), but significantly lowered levels of TNF-α (64%) (p=0.0002) and IL-6 (54%) (p=0.0002), all of which are pro-inflammatory cytokines known to be upregulated after liver injury. Levels of IL-2 did not change (p=0.43). In contrast, the concentration of soluble IL-1ra was 87% lower in MSC-CM treated animals (p=0.0002). Levels of the anti-inflammatory cytokine IL-10 were increased 4-fold in MSC-CM treated animals (p=0.032).

These studies show that infusion of supernatants from MSC downregulates the systemic inflammation typically associated with FHF.

Example 8—MSC-CM Improves Liver Pathology

Thirty-six hours after systemic treatment with concentrated MSC-CM or vehicle, livers samples of Gal-N rats were analyzed by hematoxylin & eosin (H&R) staining of paraffin embedded sections.

Microscopic evaluation of H&E stained liver sections revealed profound hepatocellular death with cytoplasmic vacuolization, panlobular mononuclear leukocyte infiltration and severe distortion of tissue architecture in vehicle-treated animals. In contrast, livers of MSC-CM treated animals demonstrated only minor periportal immune cell infiltration with edema and fibrin deposition, characteristic of tissue repair.

Figure 12A:
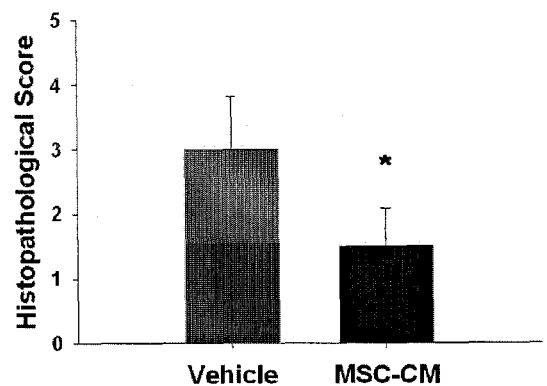
FIG. 12A is a bar graph showing scores determined by semi-quantitative histological exam as described in Example 6. Data shown are mean±standard error of the mean of 10 random high power fields per animal. Solid Bar=100 μm. $*p=0.024$, $**p=0.004$.

FIG. 12A shows semi-quantitative histological examination confirmed significant differences between the groups. The average score in the MSC-CM group was 1.5±0.6 and 3.0±0.8 for vehicle treated animals (p=0.024).

Figure 12B:
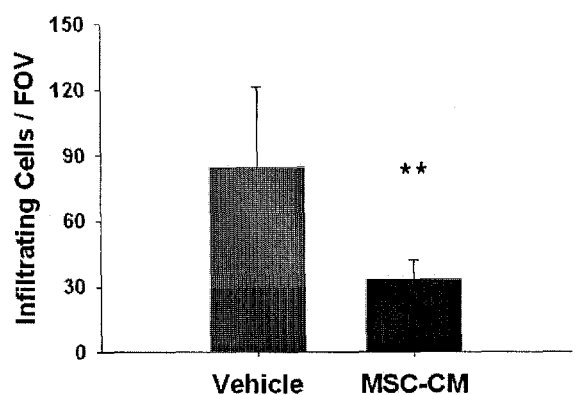
FIG. 12B is a bar graph showing quantification of infiltrating immune cells by digital image analysis. Data shown are mean±standard error of the mean of 10 random high power fields per animal. Solid Bar=100 μm. $*p=0.024$, $**p=0.004$.
Figure 13:
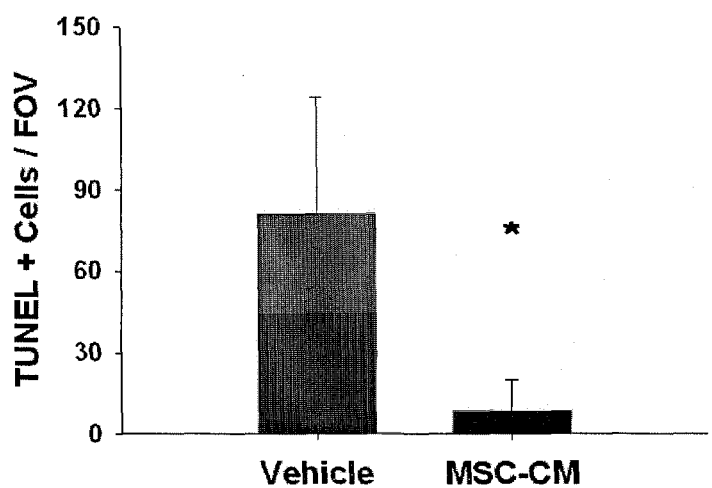
FIG. 13 is a bar graph showing the results of quantification of TUNEL-positive nuclei using digital image analysis. Data are reported as mean±standard error of the mean for 10 random fields per animal. $*p=0.009$.

Quantification of infiltrating immune cells was performed using freely available ImageJ software (rsb.info.nih.gov/ij/). As shown in FIG. 12B, a 58% decrease in the number of infiltrating immune cells was observed after MSC-CM infusion (33±9.3 compared to 84±37 in controls) (p=0.004).

These results demonstrate that MSC-CM therapy inhibits liver damage and immune cell infiltration in Gal-N induced FHF.

Example 9—MSC-CM Inhibits In Vivo Hepatocellular Apoptosis

Hepatocellular apoptosis was analyzed according to the following procedures.

Four-micron thick sections of formalin fixed liver tissue were deparaffinized and rehydrated after baking at 60° C. for 1 hour. Peroxidase activity was blocked using 3% hydrogen peroxide in ethanol for 15 minutes.

Terminal deoxynucleotidyl Transferase Biotin-dUTP Nick End Labeling (TUNEL) was performed using the APOPTAG Peroxidase In Situ Apoptosis Detection Kit (Chemicon International, Temecula, Calif.) according to the vendor's instructions. The sections were developed using 3,3'-diaminobenzidine and counter-stained with Gill's Hematoxylin.

Quantification of TUNEL-reactivity and infiltrating immune cells was performed using freely available ImageJ software (rsb.info.nih.gov/ij/). Ten random 40× images were analyzed per animal. Particles were quantified using appropriate criteria for corresponding sizes of the nuclei. Particles of area greater than 700 μm2 were analyzed to specifically identify hepatocytes from non-parenchymal and inflammatory cells.

To determine whether MSC-CM infusion decreases apoptotic cell-death, the number of TUNEL-reactive nuclei in liver sections was determined. In sections from vehicle-treated rats, many apoptotic nuclei were observed. In contrast, few TUNEL-positive nuclei were present after MSC-CM treatment. Quantification revealed a 90% reduction in TUNEL-positive nuclei (8.3±12/field of view) when compared to control animals (81±52) (p=0.009). These observations confirm that MSC-CM therapy effectively reduces hepatocellular death in this model of acute liver injury.

Example 10—MSC-CM Inhibits Hepatocyte Apoptosis In Vitro

Inhibition of hepatocellular death by MSC-CM therapy in vivo can either be a direct effect of trophic molecules preserving liver cells, or an indirect effect, for example through inhibition of the immune response. Therefore, the ability of MSC-CM to directly inhibit apoptosis was assayed in cultured hepatocytes, as follows.

Primary rat hepatocytes were isolated using a two-step collagenase perfusion procedure as described previously (Dunn et al., FASEB J., 3:174-177, 1989). The yield was routinely 200-300 million hepatocytes with viability greater than 90% as determined by trypan blue exclusion. Hepatocyte culture medium consisted of DMEM supplemented with 10% FBS 14 ng/ml glucagon, 0.5 U/ml insulin, 20 ng/ml epidermal growth factor (EGF), 7.5 µg/ml hydrocortisone, 200 µg/ml streptomycin and 200 U/ml penicillin. Culture conditions were hepatocyte medium for control experiments; hepatocyte medium mixed at a 50:1 ratio with the 25-fold concentrated MSC-CM (2% MSC-CM); and hepatocyte medium mixed at a 12.5:1 ratio for 8% MSC-CM.

Isolated primary rat hepatocytes were cultured as described above for a total of 7 days in 12-well plates at a density of $1 \times 10^5$ cells/cm$^2$ in a collagen gel sandwich configuration. Apoptosis was induced using Actinomycin D (1 hour) and TNF-α (8 hours). During exposure to TNF-α, hepatocytes were cultured in hepatocyte medium only or hepatocyte medium supplemented with 2% or 8% of 25× concentrated MSC-CM. Hepatocytes were stained using a fluorescent Live Dead Assay (Molecular Probes). Cell death was quantified using digital image analysis of 4 images per well. Experiments were performed in triplicate.

Figure 14:
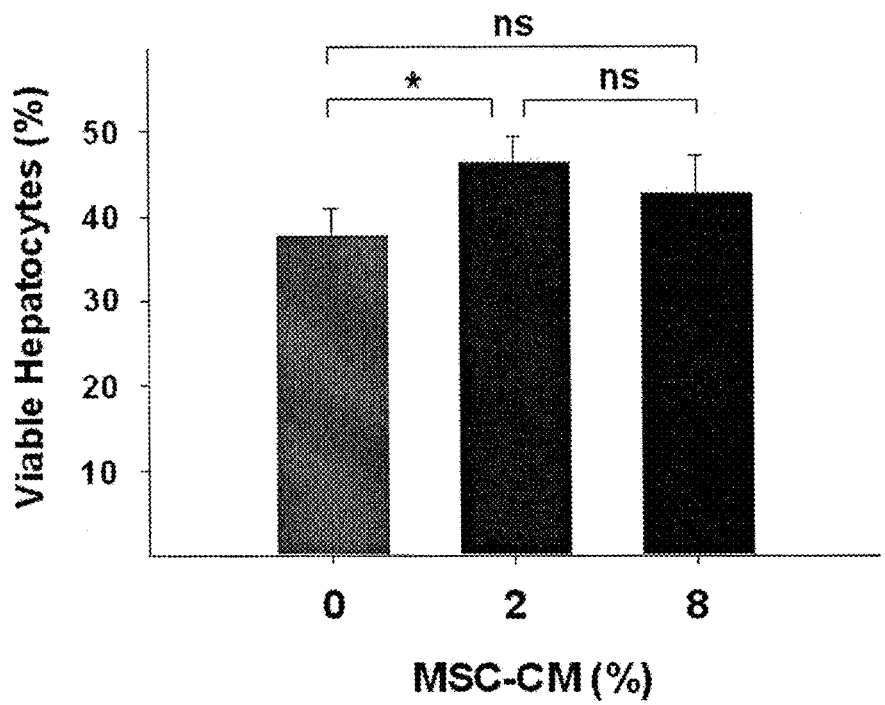
FIG. 14 is a bar graph showing isolated primary rat hepatocyte apoptosis using in vitro culture. Data are shown as mean±standard deviation. $*p=0.005$.

As shown in FIG. 14, a 22% increase in the fraction of viable cells was observed when hepatocyte medium was supplemented with 2% MSC-CM (46% viable compared to 38% viable in control cultures) (p=0.005). No significant increase in hepatocytes viability was seen with 8% MSC-CM (43%) (p=0.15). These experiments demonstrate that low level MSC-CM has a direct anti-apoptotic effect on hepatocytes. Therefore, MSC-CM is directly hepatoprotective. In other words, MSC-CM has a direct preserving effect on hepatocytes.

Rescue/protection from hepatocellular apoptosis was more prominent in vivo than in vitro. This observation is likely due to local and systemic inhibition of the apoptotic response.

Example 11—MSC-CM Enhances Liver Regeneration

Stimulation of endogenous repair programs is also a potential mechanism of the above described MSC-CM-induced therapeutic effect.

Liver samples of Gal-N rats were analyzed 36 hours after FHF induction with MSC-CM or vehicle. Proliferating cell nuclear antigen (PCNA) staining was performed by treating sections with 10 mM Citrate Buffer at pH 6.0 using a digital pressure cooker. Subsequently, sections were blocked with 1.5% horse serum for 15 minutes and incubated with mouse monoclonal anti-PCNA (Clone 24, BD Transduction Laboratories, San Jose, Calif.) at a 1:500 dilution for 1 hour at room temperature. Primary antibody was detected using Vectastain Elite ABC kit (Vector laboratories, Burlington, Calif.). Sections were developed using 3,3'-diaminobenzidine and counter-stained with Gill's Hematoxylin.

Figure 15:
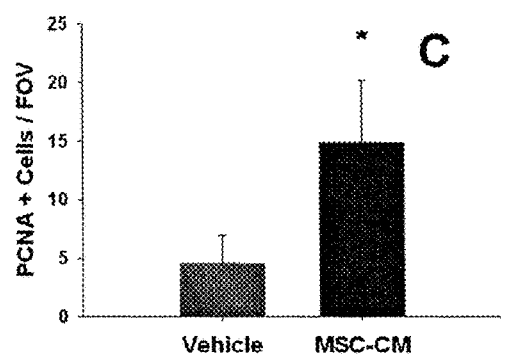
FIG. 15 is a bar graph showing PCNA-reactive nuclei were quantified by digital image analysis. Data are reported as mean±standard error of the mean for 10 random fields per animal. $*p=0.04$.

PCNA reactive cells were quantified and compared to vehicle-treated animals. As shown in FIG. 15, 3-fold more PCNA-reactive cells were observed in MSC-CM treated livers than control livers.

The mRNA expression profiles of 10 genes known to be upregulated during liver regeneration was performed using RT-PCR, as described in Example 3E. Forward and reverse oligonucleotide combinations are shown in Table 3.

TABLE 3

| | RT-PCR Oligonucleotides | | | | |
|---|---|---|---|---|---|
| Gene | SEQ ID NO: | Forward (5'-3') | SEQ ID NO: | Reverse (5'-3') | Amplicon (bp) |
| OSM | 5 | caactgggtg ctttcagaca | 6 | aacccatgaa gcgatggtag | 253 |
| AR | 7 | gtctttgtct ccgccgtaag | 8 | ctgaacttct ggagccttcg | 244 |
| TGF-α | 9 | gcaagttctg cctgttcctc | 10 | gcactgaacc aacccacttt | 161 |
| HGF | 11 | cgagctatcg cggtaaagac | 12 | tgtagctttc accgttgcag | 165 |
| TNF | 13 | actcccagaa aagcaagcaa | 14 | cgagcaggaa tgagaagagg | 211 |
| EGF | 15 | acaccgaagg tggctatgtc | 16 | tagagtcagg gcaaggcagt | 195 |
| IL-6 | 17 | ccggagagga gacttcacag | 18 | cagaattgcc attgcacaac | 134 |
| SCF | 19 | caaaactggt ggcgaatctt | 20 | gccacgaggt catccactat | 217 |
| HG-EBF | 21 | gcctcctgta attgctctgc | 22 | gccaaaaatc ctggagcata | 207 |
| TIMP3 | 23 | tgtacacccc agcctcttc | 24 | cttctcgcca agacctcaac | 182 |
| 18s | 25 | atgacatcaa gaaggtggtg | 26 | cataccagga aatgagcttg | 177 |

Figure 16:
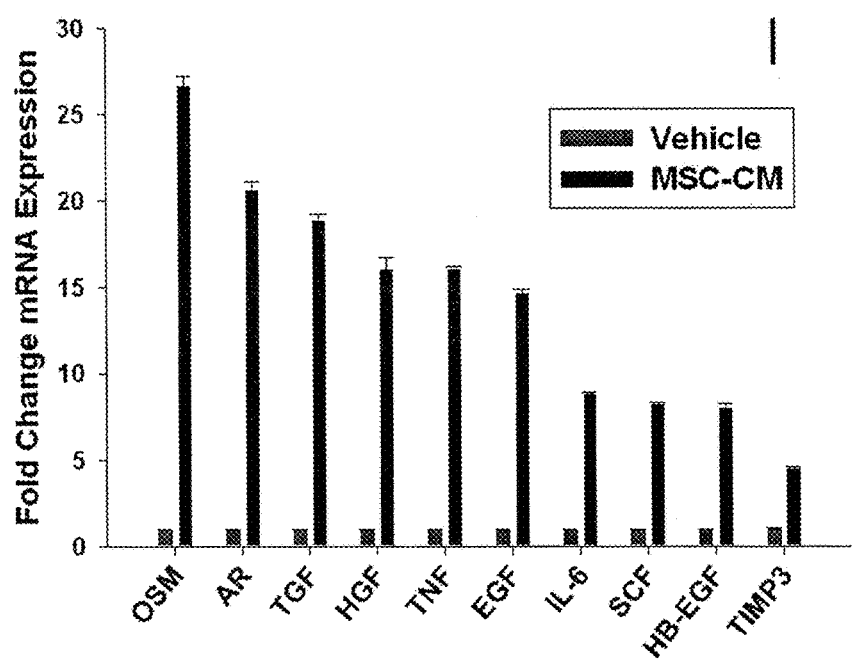
FIG. 16 is a bar graph showing the results of quantification of changes in gene expression by real time PCR (RT-PCR) after MSC-CM treatment. Abbreviations are: oncostatin M (OSM); α-1β adrenergic receptor (AR); transforming growth factor-α (TGF-α); hepatocyte growth factor (HGF); tumor necrosis factor-α(TNF-α); epidermal growth factor (EGF); interleukin 6 (IL-6); stem cell factor (SCF); heparin-binding epidermal growth factor-like growth factor (HB-EGF); and tissue metalloproteinase 3 (TIMP3).

Visibly stronger bands were observed for each of the genes analyzed. As shown in FIG. 16, this observation was confirmed using quantitative analysis. Increases ranged from 4-fold to 27-fold.

These results demonstrate that administration of MSC-derived soluble factors enhances liver regeneration programs during FHF.

Example 12—MSC-CM Stimulates Hepatocyte Proliferation In Vitro

Hepatocyte duplication, a major component of liver regeneration, is regulated by a complex interaction of paracrine and endocrine signals involving non-parenchymal liver cell types as well as extra-hepatic organs. To determine whether MSC-derived factors can directly enhance hepatocyte replication, the effect of MSC-CM on the in vitro proliferation of isolated primary hepatocytes was explored.

Primary rat hepatocytes were isolated as described in Example 9. Hepatocytes were subsequently seeded at a low density (1.25×10³ cells/cm²) on a feeder layer of 3T3 J2 fibroblasts (8×10⁴ cells/cm²) previously exposed to 12 µg/ml mitomycin-C for 2.5 hours to arrest growth. Hepatocytes were allowed to proliferate with daily medium changes. Hepatocyte culture medium is described in Example 9.

Cells were cultured with 10 µM bromodeoxyuridine (BrdU; Sigma). After 48 hours, cultures were fixed in 70% ethanol for 45 minutes and treated with 4N HCl and 0.2% TRITONX-10. Cells were then incubated in blocking buffer for 30 minutes and incubated for 60 minutes with anti-BrdU-Alex594 (Invitrogen, Carlsbad, Calif.) and rabbit anti-rat albumin (ICN Pharmaceuticals, Aurora, Ohio) at 37° C., followed by FITC conjugated anti-rabbit IgG (ICN Pharmaceuticals) at room temperature. BrdU positive cells in each hepatocyte colony were counted in fluorescence microscopy images. Albumin content in supernatant samples was determined by an enzyme-linked immunosorbent assay (ELISA) using purified rat albumin and a peroxidase-conjugated anti-albumin antibody (MP Biomedicals, Aurora, Ohio). Urea content was determined with a commercially available kit (StanBio Laboratory, Boerne, Tex.) according to the vendor's instructions.

Figure 17A:
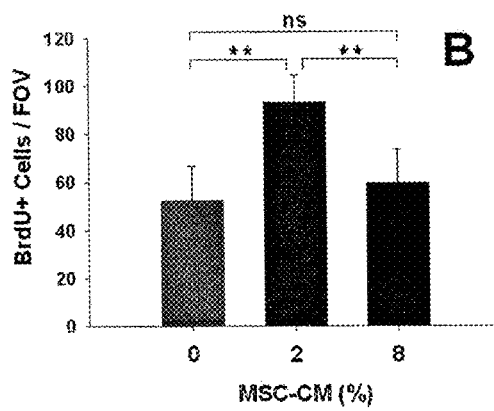
FIG. 17A is a bar graph showing quantification of BrdU-positive hepatocytes by image analysis. Data are shown as mean±standard deviation of two separate experiments in duplicate. $*p<0.05$, $**p<0.01$; ns=not significant.

Proliferation of rat hepatocyte colonies on a feeder layer of growth-inhibited 3T3-fibroblasts as visualized by double immunofluorescence staining for BrdU and albumin. As shown in FIG. 17A, with 2% MSC-CM supplementation (represented in graph as 2), a 79% increase in BrdU-positive hepatocytes was observed (9 3±12 per field of view with MSC-CM vs. 52±14 in control cultures) (p=0.001). When medium was supplemented with 8% MSC-CM (shown in graph as "8"), no significant increase was measured (59±14 BrdU) (p=0.37).

Figure 17B:
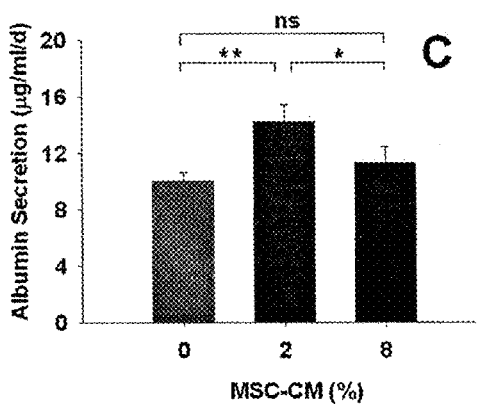
FIG. 17B is a bar graph showing albumin secretion. Data are shown as mean±standard deviation of two separate experiments in duplicate. $*p<0.05$, $**p<0.01$; ns=not significant.

As shown in FIG. 17B, in parallel to these findings, the total amount of albumin secreted and urea synthesized per well was increased in 2% MSC-CM supplemented cultures. Albumin levels were 29±2.4 µg/ml/day, compared to 20±1.2 µg/ml/d under control conditions (p=0.006). No significant difference compared to control was observed in 8% MSC-CM conditions (23±2.2 µg/ml/d) (p=0.14).

Figure 17C:
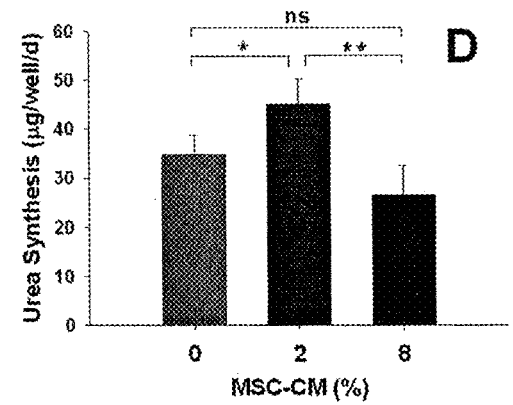
FIG. 17C is a bar graph showing urea synthesis. Data are shown as mean±standard deviation of two separate experiments in duplicate. $*p<0.05$, $**p<0.01$; ns=not significant.

As shown in FIG. 17C, urea synthesis shifted from 69±8.1 µg/ml/d in control cultures to 90±10 µg/ml/d in 2% MSC-CM conditions (p=0.019), but was not significantly altered in the presence of 8% MSC-CM (53.1 µg/ml/d) (p=0.063).

In general, therefore, markers of hepatocyte proliferation and function were significantly higher in the presence of 2% MSC-CM in vitro. Although 8% MSC-CM also had an effect on hepatocyte proliferation and function in vitro, it was not as pronounced as those levels observed with 2% MSC-CM.

The data presented herein clearly demonstrates that MSC-CM is capable of increasing hepatocyte proliferation. MSC-CM increased the number of proliferating cells at least 3-fold in the regenerating, injured liver. MSC cells are not required for the observations described above. Secreted factors contained in MSC-CM are sufficient in protecting hepatocytes from apoptosis and promoting hepatocyte proliferation. Thus, systemic infusion of MSC-CM represents an effective strategy for MSC therapy.

Example 13—MSC-Derived Factors Reverse Fulminant Hepatic Failure

This example demonstrates that MSC-derived molecules provide survival benefits against parenchymal cell loss, wherein cell loss is integrated with a local and systemic immune response, following intravenous bolus administration of MSC-CM and/or extracorporeal perfusion with a bioreactor containing MSCs (e.g., undifferentiated MSCs).

Sprague-Dawley rats were intraperitoneally administered a total of two injections of 1.2 g/kg of a hepatotoxin, D-galactosamine (Gal-N), each separated by 12 hours, as described in Example 5.

Animals treated 24 hours later with intravenous injections into the penile vein of (1) whole MSCs or (2) MSC lysates. MSCs were isolated and characterized as described in Examples 1 and 2.

A total of 2×10⁶ cells were administered to each subject for whole cell MSC therapy. The volume of whole MSCs was 500 µl.

Cell lysates were prepared by sonication. The dose of sonicated cells administered was 2×10⁶ cells per subject. The volume of MSC lysate was 500 µl. Unlike MSC-CM, MSC lysate is not concentrated.

Vehicle (PBS) and NIH 3T3-J2 fibroblast cell lysate were administered as controls. The volume of each control was 500 µl.

As shown in FIG. 18, no significant benefit was seen after the intravenous infusion of 2×10⁶ human MSCs. This observation is most likely due to poor engraftment, entrapment in the alveolar capillary bed, and/or immune rejection of the cells. In contrast, treatment with cellular lysates, derived from the same cell mass used for transplantation, showed an increased survival trend compared to vehicle (P<0.47) and fibroblast lysate (P<0.36) controls.

Example 14—MSC-Derived Components Reverse FHF

The experiments described in this example demonstrate that MSC-derived components promote survival in FHF-models and that this effect is not species specific, e.g., the therapeutic potential of MSC-CM is not species specific.

Figure 19B:
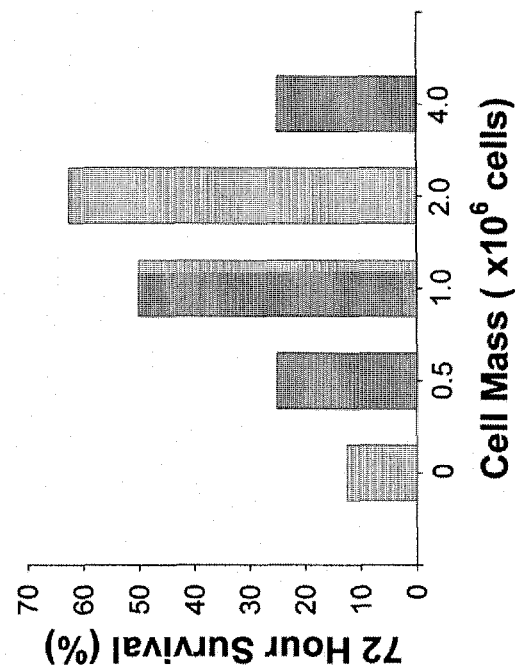
FIG. 19B is a bar graph showing dose response of animal survival 72 hours after liver failure induction as a function of MSC mass from which MSC-CM was derived. Controls received vehicle or fibroblast conditioned medium (fibroblast-CM). Time points of interventions are stated above survival plots. Results for both panels are cumulative data of two independent experiments using different batches of MSC-CM (N=8 per each group). P-value determined by Log Rank Test.
Figure 19A:
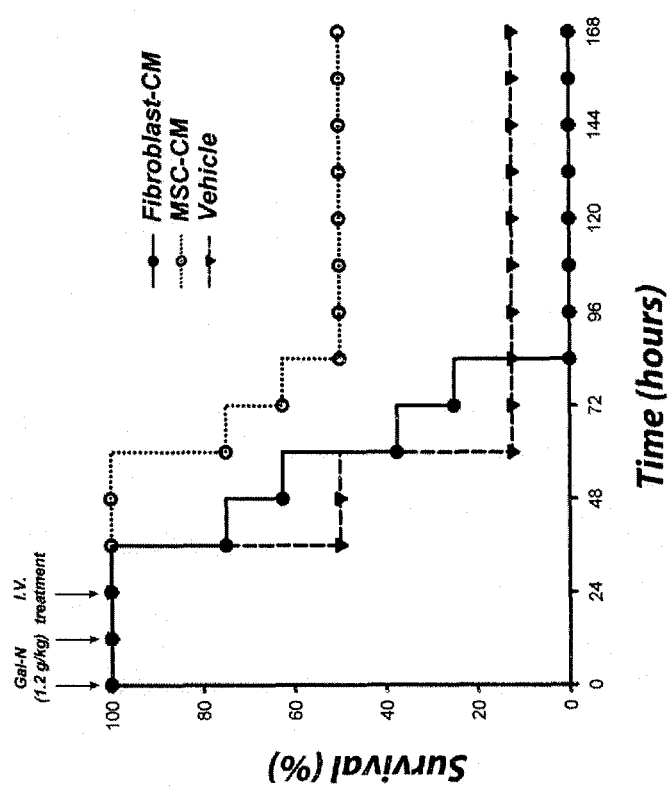
FIG. 19A is a line graph showing Kaplan-Meier survival analysis of Gal-N administered rats treated with concentrated MSC-CM.

As shown in FIG. 19A, a longitudinal study using MSC-CM from 2×10⁶ human MSCs revealed a distinct survival benefit compared to vehicle (P<0.032) and fibroblast (P<0.026) concentrated medium.

72 hour survival of FHF-induced rats was monitored as a function of MSC mass from which MSC-CM was collected. As shown in FIG. 19B, MSC-CM was most effective when derived from a MSC mass of 2×10⁶ cells.

The observation that xenogeneic MSC lysates and supernatants decreased animal mortality suggests that these factors can cross species barriers. Thus, the therapeutic potential of MSC-CM is not species-specific.

Example 15—Combined Metabolic and Secretory Function in MSC-EB Provide Hepatoprotection and Survival Benefit A MSC-extracorporeal bioreactor (MSC-EB) was developed to combine the effectiveness of MSC whole cells and MSC-CM in a single device.

Extracorporeal device operation was previously reported (Shinoda et al., J. Surg. Res., 137:130-140, 2007). Briefly, male Sprague-Dawley rats weighing between 280 and 370 grams were anaesthetized using intraperitoneal injections of ketamine and xylazine at 110 and 0.4 mg/kg, respectively. The left carotid artery and right jugular vein were cannulated and the animal was placed in a metabolic cage. Twenty-four hours later, 1.2 g/kg Gal-N freshly dissolved in physiological saline and adjusted to pH 7.3 with 1 N NaOH was injected i.p., followed by a second equal injection 12 hours later, as described in Example 5. Twenty-four hours after the first injection of Gal-N, the arterial and venous lines were connected to an extracorporeal circuit. Plasma was separated using a plasma separator (MicroKros, pore size 0.2 micron). Plasma was perfused through the polycarbonate, flat-plate bioreactor and subsequently reunited with the cellular components of the blood and returned to the animal. The extracorporeal bioreactor was operated for 10 hours. Animals that died during reactor operation and failed to receive adequate treatment (MSC-EB, N=3 and Fibroblast-EB, N=2) were censored from analysis. Animal survival was monitored every 12 hours. Plasma or whole blood was analyzed for liver injury biomarkers (e.g., serum alanine aminotransferase (ALT), serum aspartate aminotransferase (AST)) using a microfluidic metabolic assay (Picollo, Abaxis, Union City, Calif.). An exemplary schematic representation of an extracorporeal circuit is shown in FIG. 20.

Figure 21A:
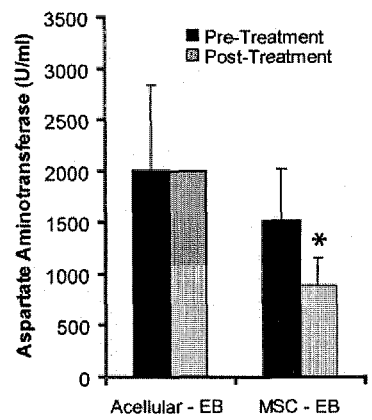
FIGS. 21A-21B are bar graphs showing data collected from extracorporeal bioreactor (EB) studies. Animals were treated with an MSC-EB, using a 3T3 fibroblast-based bioreactor (fibroblast-EB) and an acellular bioreactor (acellular-EB) as controls. Serum biomarkers of liver injury, aspartate aminotransferase (AST, 21A) and alanine aminotransferase (ALT, 21B) preceding and 24 hours after treatment with a MSC-EB (n=5) or an acellular-EB (n=3). Due to mortality, n=1 in the acellular group after treatment. P-value determined by student's t-test analysis.
Figure 21B:
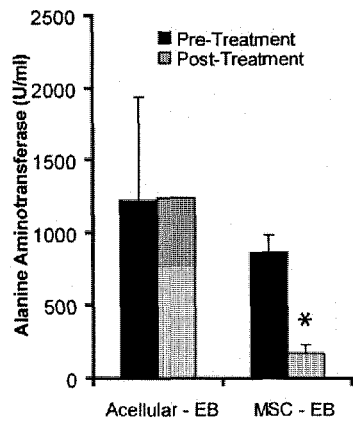
Figure 21C:
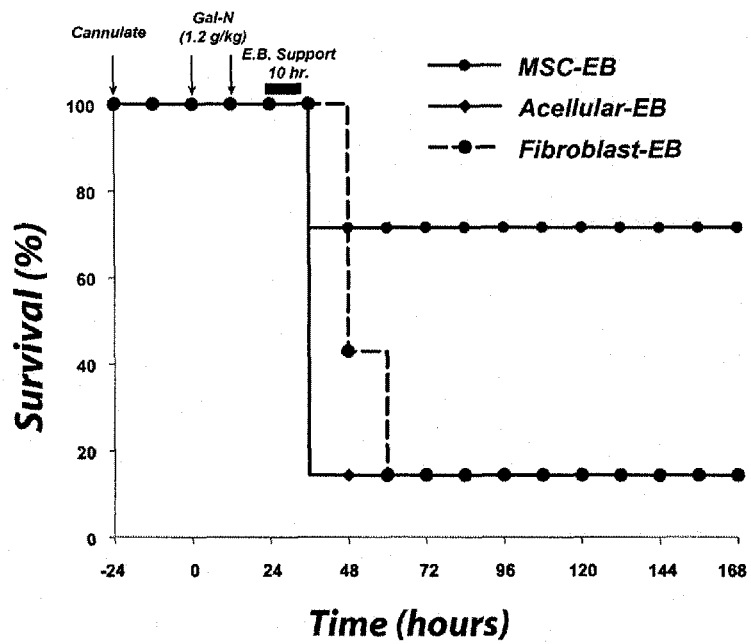
FIG. 21C is a line graph showing the results of Kaplan-Meier survival analysis of Gal-N administered rats treated with EBs. Time points of interventions are stated above survival plots. Each result shown was from an independent experiment using different batches of MSCs. P-value determined by Log Rank Test.

Animals were treated 24 hours after FHF induction with a human MSC-EB connected to the systemic circulation of the animal. Bioreactors seeded with fibroblasts (fibroblast-EB) and acellular (acellular-EB) bioreactors served as controls. After 10 hours of extracorporeal perfusion, animals were taken off assist support and monitored for survival. Plasma was obtained at the start of, and 24 hours after, bioreactor treatment and analyzed for hepatocyte enzyme release. As shown in FIGS. 21A-B, liver serologies, including aspartate aminotransferase (AST; $P<0.02$) and alanine aminotransferase (ALT; $P<0.001$) were improved in animals treated with the MSC-EB. These data demonstrate a hepatoprotective effect of device therapy as shown by the reduction in biochemical markers of hepatocyte death. As shown in FIG. 21C, 71% of animals treated with the MSC-EB survived, compared to 14% in both acellular ($P<0.037$) and fibroblast controls ($P<0.05$). Table 5 shows liver serologies after MSC-EB treatment.

TABLE 5

Liver Serologies are Improved after MSC-EB Treatment

| Parameter | MSC | Pre MSC-EB | Post MSC-EB (24 hr) | Post MSC-EB (48 hr) | % Change |
|---|---|---|---|---|---|
| TB | − | 0.73 ± 0.75 | 0.9 | N/A | +23 |
| (mg/dl) | + | 0.76 ± 0.26 | 1.16 ± 0.83 | 1.2 ± 0.84 | +58 |
| AST | − | 2007 ± 837.4 | 1999 | N/A | 0 |
| (U/l) | + | 1513.2 ± 513.2 | 888 ± 272.6 | 940.8 ± 330.53 | −41 |
| ALT | − | 1222.33 ± 710.4 | 1233 | N/A | 0 |
| (U/l) | + | 859.2 ± 125.7 | 168 ± 61.9 | 358.8 ± 198.4 | −80 |
| ALP | − | 216 ± 39.1 | 106 | N/A | −51 |
| (U/l) | + | 192.8 ± 41 | 91.2 ± 23.2 | 98.4 ± 24.6 | −53 |

Data are expressed as mean ± standard error of the mean (SEM). Percent change refers to post MSC-EB (24 hours) relative to pre MSC-EB. (−) is EB without MSCs. N = 5 for (−). N = 3 for (+). No data acquired due to mortality (N/A).

As shown in Table 5, liver serologies were improved after MSC-EB treatment.

Example 16—MSC-CM Therapy Inhibits Panlobular Leukocyte Invasion, Bile Duct Duplication, and Hepatocellular Death Post MSC-CM histopathological changes were evaluated using a sub-lethal Gal-N regimen (0.6 g/kg) to induce acute liver injury, while ensuring survival in our control-treated group for comparison. It should be noted that even at this Gal-N dose, mortality occurred in a vehicle-treated group (N=1). This confirms that the extent of injury in this model can still be fatal. Gal-N injured rats were treated with vehicle (N=4) or MSC-CM (N=4) 24 hours after injury and their livers were harvested 36 hours thereafter for pathological analysis.

Liver tissue was harvested from rats induced with a sub-lethal regimen of Gal-N (0.6 g/kg), 36 hours after treatment with MSC-CM. Tissue was fixed in 10% buffered formalin, embedded in paraffin, sectioned to 6-μm thickness, and stained with hematoxylin and eosin.

Microscopic evaluation of liver tissue from vehicle treated rats revealed profound hepatocellular apoptosis, bile duct duplication and panlobular mononuclear leukocyte infiltration with cytoplasmic vacuolization and severe distortion of tissue architecture. MSC-CM treated rats showed no signs of disseminated inflammation, although minor periportal infiltration with edema and fibrin deposition consistent with tissue repair was observed.

Histopathology was scored using the criteria described in Example 6 ("0" for normal histology, "1" for minor hepatocellular death and inflammation, "2" for widely distributed patchy necrosis with inflammation, "3" for complete lobular disruption and diffuse hepatocyte necrosis with panlobular inflammation, and "4" for mortality). Clearly, MSC-CM treated livers presented a lower score than vehicle treated livers.

Lower numbers of infiltrating leukocytes were observed in MSC-CM treated livers.

Example 17—MSC-CM Alters Immune Cell Migration to the Liver

To investigate whether the lack of panlobular leukocyte infiltration observed in MSC-CM treated livers may be due to the MSC-CM-dependent diversion of immune cell migration away from an inflamed, target organ, radiolabeled leukocytes were adoptively transferred directly after MSC-CM or vehicle treatment, into Gal-N (0.6 g/kg) injured rats. Briefly, leukocytes were isolated from whole rat blood by NH4Cl erythrocyte lysis. Cells were pelleted, washed once with PBS and resuspended in 0.9% saline containing the In111 oxine isotope (GE Healthcare Biosciences Corp., Piscataway, N.J.). Cells were labeled at 92% efficiency with high viability. Approximately $15 \times 10^6$ cells were infused into the penile vein of Gal-N injured (0.6 g/kg) directly after treatment with vehicle or MSC-CM.

Figure 22A:
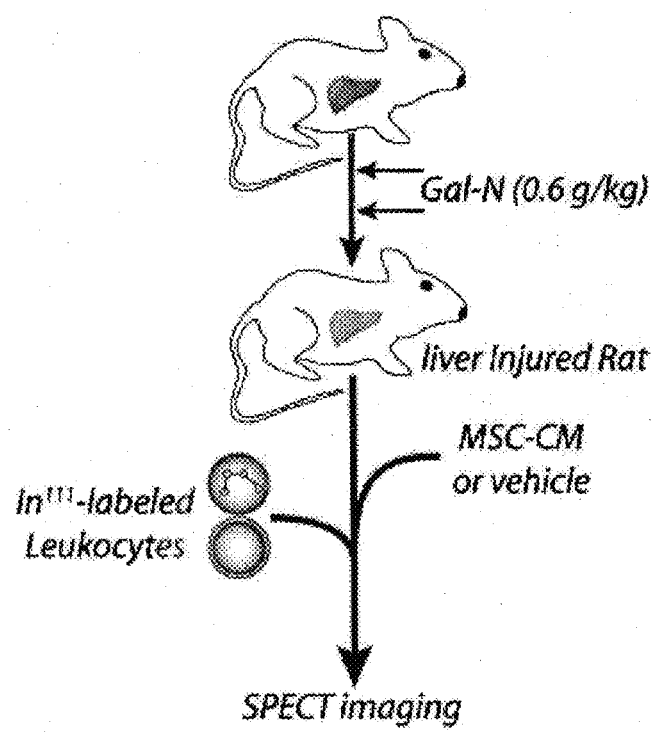
FIG. 22A is a schematic illustration of the experimental design of an adoptive transfer study. Gal-N injured rats were treated with vehicle or MSC-CM followed by infusion of $In^{111}$-labeled leukocytes.

Leukocyte trafficking was then monitored in these animals using single photon emission computed tomography (SPECT) over time. SPECT images were captured using a M.CAM gamma camera setup (Siemens Medical Systems, Malvern, Pa.) at 0, 3 and 24 hours after leukocyte infusion. An illustration of this protocol is provided in FIG. 22.

Qualitatively, more leukocytes were seen migrating to the liver in vehicle treated animals over time. In contrast, there was a distinct decrease in signal intensity in the liver of MSC-CM treated animals over time. These results suggest that there was a selective pressure upon leukocytes to emigrate from the liver due to MSC-CM, unlike control conditions where leukocytes eventually migrated to the injured organ.

Figure 22B:
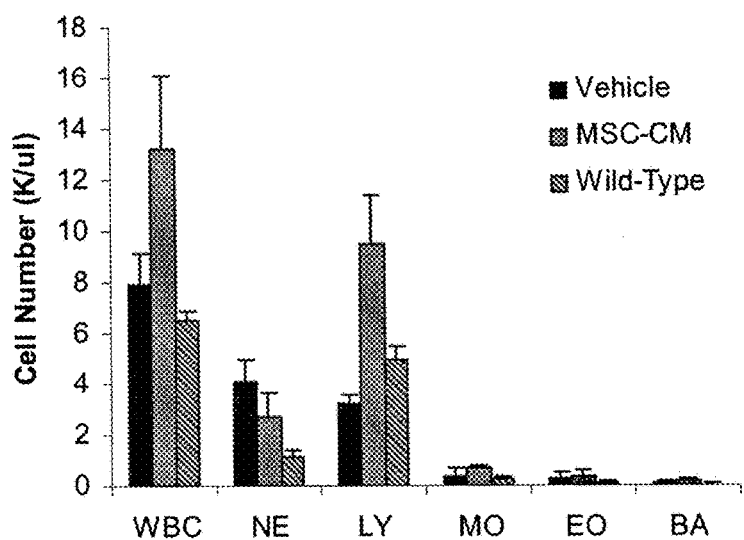
FIG. 22B is a bar graph illustrating leukocyte count and differentials. Whole blood was harvested after cannulation and analyzed for peripheral blood cells using a commercially available flow cytometer (white blood cells (WBC); neutrophils (NE); lymphocytes (LY); monocytes (MO); basophils (BA); eosinophils (EO).

As shown in FIG. 22B, in rats administered a sub-lethal dose of Gal-N (0.6 mg/kg), dramatic changes in leukocyte counts and differentials were observed in peripheral blood cell populations in MSC-CM treated animals.

Leukocyte distribution was also evaluated at the organ level. Animals were sacrificed at 0.5 hour, 8 hour, and 24 hour time points. Leukocyte levels were determined for indicated organs using scintillation counts.

Figure 22C:
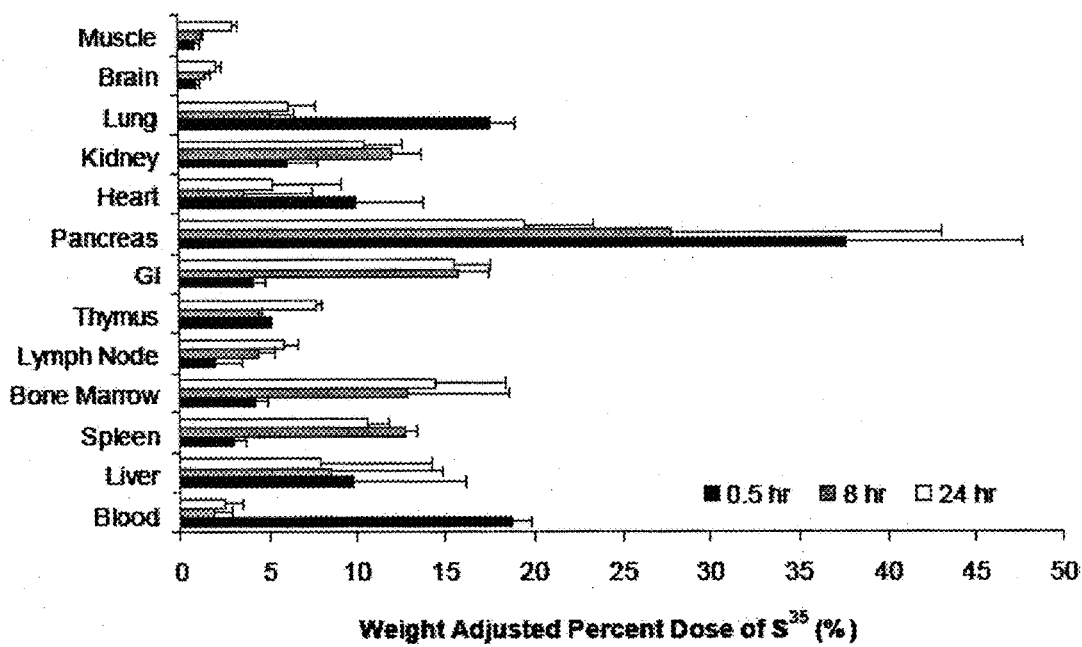
FIG. 22C is a bar graph showing the in vivo distribution of radiolabeled leukocytes following sub-lethal Gal-N treatment.

As shown in FIG. 22C, lymphoid organs and the liver are the primary sites of MSC-CM activity (50% of total solid organs at 24 hours). Considerable MSC-CM activity was, however, observed in every organ analyzed.

These data support the notion that altered leukocyte migration may be a potential target of MSC-CM therapy. These data also support the systemic use of MSC-CM therapy, e.g., for the treatment of multi-organ failure in a subject. Thus, MSC-CM therapy may provide a beneficial effect in the following organs, the lung, the heart, the pancreas, the GI, the thymus, the lymph node, bone marrow, the spleen, the liver, and the blood.

Example 18—MSC-CM Characterization

In an effort to understand the molecular mediators of the observed effects of MSC therapy, we examined MSC-CM using a high-density protein array.

Briefly, MSC supernatants were prepared by collecting serum-free medium after 24 hour culture of approximately $2 \times 10^6$ MSCs. Supernatants were analyzed for a panel of specified proteins using an antibody array (RAYBIO Human Cytokine Antibody Array C Series 2000, RayBiotech Inc., Norcross, Ga.) as specified by the vendor.

As shown in FIG. 23A, MSC-CM contained 69 of the 174 proteins assayed, which included a broad spectrum of molecules involved in immunomodulation and liver regeneration. As shown in FIG. 23B. cluster analysis revealed that a large fraction (30%) of MSC-CM was composed of chemokines, many of which were expressed at high levels.

MSC-CM was then fractionated based on functionality using affinity-based methods rather than other arbitrary molecular criteria such as size or hydrophobicity, as follows. MSC-CM was passed over an affinity column impregnated with heparin sulfate, a known ligand for all chemokines and separated into bound and unbound fractions. Each fraction was infused into FHF-induced rats with overall survival as the study endpoint.

As shown in FIG. 23C, the therapeutic activity of MSC-CM was restricted to the heparin bound fraction, providing a strong correlation between chemokines and the survival benefit after MSC-CM infusion in FHF-induced rats.

MSC-CM did not increase mRNA levels of the transcription factor Foxp3 in peripheral blood mononuclear cells. Foxp3 expression is restricted to regulatory T cells, an endogenous suppressor lymphocyte population.

MSC-CM is chemotactically active, while Fibroblast-CM is inert. This was evaluated using a microfluidic chemotaxis chamber previously described (Jeon et al., Nat. Biotech., 20:826-830, 2002). Neutrophils exposed to Fibroblast-CM do not show morphological changes involved with chemotaxis, whereas neutrophils exposed to MSC-CM have prominent filopodial extensions and are chemotactically primed.

Figure 24:
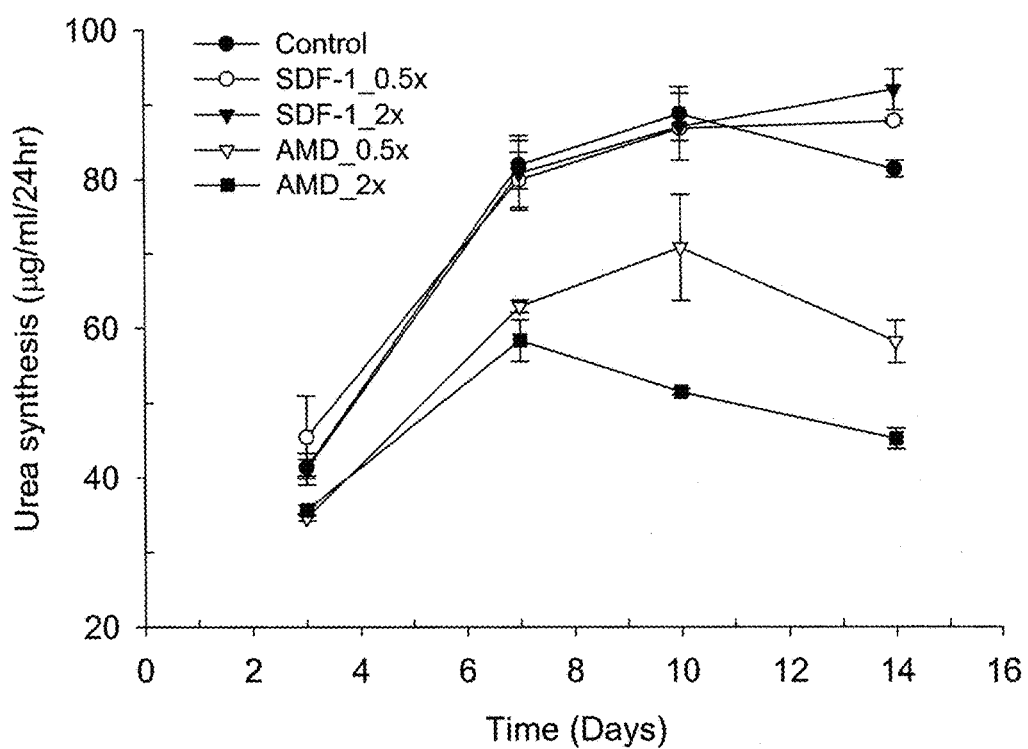
FIG. 24 is a bar graph of Urea synthesis in hepatocytes cultured on growth-arrested NIH-3T3-J2 fibroblasts for 14 days supplemented with 5 ng/ml SDF-1a or AMD3100, a CXCR4 antagonist. Data represent mean±standard error of the mean (s.e.m.) of two independent experiments performed in triplicate.

One component of MSC-CM that may be responsible for increased hepatocyte replication is SDF-1a. Hepatocytes were proliferated using aforementioned techniques in standard culture medium alone or supplemented with 5 ng/ml SDF-1a (FIG. 29B) or the SDF-1a receptor antagonist, AMD3100 at 1 uM. Increased SDF-1a stimulation led to larger colonies, while blockade of SDF-1a signaling led to smaller colonies. FIG. 24 shows urea synthesis in SDF-1a and AMD3100 treated cells. Urea synthesis is a surrogate biomarker for hepatocyte mass; the results show significant differences between control conditions and modulation of the SDF-1a signaling pathway.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of preparing a composition for the treatment of liver disease, the method comprising:
   (i) obtaining a population of undifferentiated multipotent stromal cells (MSCs);
   (ii) culturing the MSCs in a medium;
   (iii) obtaining the medium resulting from the culturing of (ii);
   (iv) fractionating the medium obtained in (iii);
   (v) selecting a fraction of the medium that is capable of one or both of promoting hepatocyte proliferation or inhibiting hepatocyte death; and
   (vi) formulating the selected fraction to form a composition for administration to a mammal.

2. The method of claim 1, wherein the composition is concentrated 25-fold.

3. The method of claim 2, wherein the medium comprises a serum free tissue culture medium.

4. The method of claim 1, further comprising lyophilizing the composition.

5. A method of preparing a composition for the treatment of liver disease, the method comprising:
   (i) obtaining a population of undifferentiated multipotent stromal cells (MSCs);
   (ii) culturing the MSCs in a medium;
   (iii) obtaining the medium resulting from the culturing of (ii);
   (iv) formulating a selected fraction of the medium obtained in (iii) to form a composition for administration to a mammal wherein the fraction has been selected based on its capability of one or both of promoting hepatocyte proliferation or inhibiting hepatocyte death.

* * * * *